(12) United States Patent
Chait et al.

(10) Patent No.: US 6,642,059 B2
(45) Date of Patent: Nov. 4, 2003

(54) METHOD FOR THE COMPARATIVE QUANTITATIVE ANALYSIS OF PROTEINS AND OTHER BIOLOGICAL MATERIAL BY ISOTOPIC LABELING AND MASS SPECTROSCOPY

(75) Inventors: Brian T. Chait, N.Y., NY (US); David Cowburn, Westfield, NJ (US); Yoshi Oda, Ibaraki (JP)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/949,510

(22) Filed: Sep. 6, 2001

(65) Prior Publication Data

US 2003/0077840 A1 Apr. 24, 2003

Related U.S. Application Data

(62) Division of application No. 09/304,799, filed on May 4, 1999, now Pat. No. 6,391,649.

(51) Int. Cl.[7] .............................................. G01N 24/00

(52) U.S. Cl. ........................ 436/173; 436/174; 436/177

(58) Field of Search ................................ 436/173, 174, 436/177

(56) References Cited

U.S. PATENT DOCUMENTS

| | | | |
|---|---|---|---|
| 4,446,237 A | 5/1984 | Berninger | |
| 4,977,320 A | 12/1990 | Chowdhury et al. | |
| 5,045,694 A | 9/1991 | Beavis et al. | |
| 5,245,186 A | 9/1993 | Chait et al. | |
| 5,338,686 A | 8/1994 | Hellerstein | |
| 5,366,721 A | 11/1994 | Turteltaub et al. | |
| 5,376,355 A | 12/1994 | Turteltaub et al. | |
| 5,453,247 A | 9/1995 | Beavis et al. | |
| 5,572,024 A | 11/1996 | Gray et al. | |
| 5,800,979 A | 9/1998 | Kolhouse et al. | |
| 6,391,649 B1 * | 5/2002 | Chait et al. | 436/173 |

OTHER PUBLICATIONS

Marshall et al., "Protein Molecular Mass to 1 Da by 13C, 15N Double–Depletion and FT–ICR Mass Spectrometry" (1997) J. Am. Chem. Soc., 119(2), 433–434.*

Tang et al., "Two–Dimensional Analysis of Recombinant *E. coli* Proteins Using Capillary Isoelectric Focusing Electrospray Ionization Mass Spectrometry" (1997) Anal. Chem., 69(16), 3177–3182.*

Yang et al., "Capillary Isoelectric Focusing–Electrospray Ionization Fourier Transform Ion Cyclotron Resonance Mass Spectrometry for Protein Characterization" (1998) Anal. Chem., 70(15), 3235–3241.*

McCormack et al., Direct Analysis and identification of proteins in mixture . . . , (1997), Anal. Chem., vol. 69, pp. 767–776.

Pasa–Tolic et al., High Throughput Proteome–wide . . . , (1999), JACS, vol. 121, pp. 7949–7950.

Jensen et al., Probing Proteome using capillary isoelectric focusing . . . , (1999), Anal. Chem., vol. 71, pp. 2076–2084.

Hellerstein and Neese, Mass isotopomer distribution analysis at eight years . . . , (1999), Am. J. Physiol, vol. 276, pp. E1146–E1170.

Oda et al., Accurate quantitation of protein expression and site–specific phosphorylation, (1999), PNAS, vol. 96, pp. 6591–6596.

Langen, H., et al. ABRF '99 Bioinformatics and Biomolecular Technologies Linking Genomes, Proteonomes and Biochemistry, An International Symposium Sponsored by the Association of Biomolecular Resource Facilities, "Combination of Mass Spectrometry and 2D Electrophoresis–Powerful Tools for Biological Experiments" (Abstract S32), Mar. 19–22, 1999.

Arnott, D., et al., "Rapid identification of comigrating gel–isolated proteins by ion trap–mass spectrometry", Electrophoresis 1998, 19, pp. 968–980.

Zhang, W. and Chait, B.T., "Protein Identification by Database Searching: A Bayesian Algorithm", 43rd ASMS Conference on Mass Spectrometry and Allied Topics, 1995, p. 643.

Wu, C., et al, "Cell Cycle– and Cln2p–Cdc28p–dependent Phosphorylation of the Yeast Stre20p Protein Kinase", The Journal of Biological Chemistry, vol. 273, No. 43, Oct. 23, 1998, pp. 28107–28115.

(List continued on next page.)

*Primary Examiner*—Jon P. Weber
(74) *Attorney, Agent, or Firm*—Hoffmann & Baron, LLP; Irving N. Feit

(57) ABSTRACT

The present invention is a method for accurately comparing the levels of cellular components, such as proteins, present in samples which differ in some respect from each other using mass spectroscopy and isotopic labeling. A first sample of biological matter, such as cells, is cultured in a first medium and a second sample of the same biological matter is cultured in a second medium, wherein at least one isotope in the second medium has a different abundance than the abundance of the same isotope in the first medium. One of the samples is modulated, such as by treatment with a bacteria, a virus, a drug, hormone, a chemical or an environmental stimulus. The samples are combined and at least one protein is removed. The removed protein is subjected to mass spectroscopy to develop a mass spectrum. A ratio is computed between the peak intensities of at least one closely spaced pair of peaks to determine the relative abundance of the protein in each sample. The protein is identified by the mass spectrum or through other techniques known in the art. Modifications to the proteins, such as the phosphorylation of the protein, and the site of the modification may also be determined through the process of the present invention. The method is applicable to the components of any type of biological matter which are ionizable and may therefore be analyzed by mass spectroscopy.

16 Claims, 12 Drawing Sheets

OTHER PUBLICATIONS

Fenyo, D., et al., "Protein identification using mass spectrometric information", Electrophoresis 1998, 19, pp. 998–1005.

Oehlen, L.J.W.M., et al., "Potential Regulation of Ste20 Function by the Cln1–Cdc28 and Cln2–CDc28 Cyclin–independent Protein Kinases", The Journal of Biological Chemistry, vol. 273, No. 39, Sep. 25, 1998, pp. 25089–25097.

James, P., "Protein identification in the post–genome era: the rapid rise of proteomics", Quarterly Review of Biophysics 30, 4 (1997), pp. 279–331.

Anderson, N.G., et al, "Twenty years of two–dimensional electrophoresis; Past, present and future", Electrophoresis, 1996, 17, pp. 443–453.

Anderson, N.L., et al, "Simultaneous Measurement of Hundreds of Liver Proteins: Application in Assessment of Liver Function", Toxicologic Pathology, vol. 24, No. 1, pp. 72–76.

Cross, F.R., Starting the cell cycle: what is the point?, Current Biology Ltd., pp. 790–798.

Oehlen, L.J.W.M., et al., "$G_1$ cyclins CLN1 and CLN2 repress the mating factor response pathway at Start in the yeast cycle", Genes & Development, 8:1058–1070, 1994, pp. 1058–1086.

Gosser, Y.Q. et al., "The solution structure of Ab1 SH3, and its relationship to SH2 in the SH(32) construct", Current Biology Ltd., pp. 1075–1086.

DeLeenheer, A., et al., "Applications of isotope dilution–mass spectrometry in clinical chemistry, pharmacokinetics, and toxicology", Mass Spectrometry Reviews, 1992, 11, pp. 249–307.

Chait, B.T., et al., "Weighing Naked Proteins: Practical, High Accuracy Mass Measurement of Peptides and Proteins", Science, Sep. 25, 1992, vol. 257, pp 1885–1894.

Anderson, N.L., et al., "Covalent Protein Modifications and Gene Expression Changes in Rodent Liver following an Administration of Methapyrilene: A Study Using Two–Dimensional Electrophor4esis", Fundamental and Applied Toxivcology, 18, pp. 570–580 (1992).

Anderson, N.L., et al., "Global Approaches to Quantitative Analysis of Gene–Expression Pattern Observed by Use of Two–Dimensional Gel Electrophoresis", Clinical Chemistry, vol. 30, No. 12, 1984, pp. 2031–3036.

Grostic, M.F., et al., "Mass–Spectral Studies Employing Stable Isotopes in Chemistry and Biochemistry", appearing in *Mass Spectroscopy: Techniques and Applications* edited by Milne, G.W.A., Wily–Interscience, 1971, pp. 217–287.

* cited by examiner

FIG. 5 Abl-SH2, 1pmole (40%)

FIG. 6 Abl-SH2, 1 pmole (40%)

FIG. 7 LINEARITY (R=0.997)

METHOD FOR THE COMPARATIVE QUANTITATIVE ANALYSIS OF PROTEINS AND OTHER BIOLOGICAL MATERIAL BY ISOTOPIC LABELING AND MASS SPECTROSCOPY

This application claims priority to U.S. patent application Ser. No. 09/304,799 now U.S. Pat. No. 6,391,649, filed May 4, 1999, which is incorporated herein by reference.

STATEMENT AS TO RIGHTS TO INVENTIONS MADE UNDER FEDERALLY-SPONSORED RESEARCH AND DEVELOPMENT

The U.S. Government has certain rights to the invention, by virtue of its partial support of research under National Institute of Health Grant Nos. RR00862 (BTC), GM47021 and GM49716 (FRC).

FIELD OF THE INVENTION

The invention relates to the analysis of biological matter and, more particularly, to the comparison of isotopically labeled components of biological matter from one sample with the same, unlabeled components of biological matter from another sample, through mass spectroscopy. The method is particularly suited for quantifying differences in protein expression or modification in two cell populations or pools, one of which is subjected to environmental, genetic or chemical modulation.

BACKGROUND OF THE INVENTION

Many biological processes in living cells are controlled by alterations in the levels or states of certain key proteins. Measuring the levels of the various proteins that affect (or are affected by) the process is therefore important for gaining an understanding of the biological process. For example, a given hormone may, through a signaling cascade, activate certain key transcription factors which in turn induce the expression of a number of proteins with distinct activities. Comparison of the levels of the proteins in the cell prior to and after induction can indicate which gene products are being up regulated and/or down regulated by the action of the hormone. As a second example, comparison of the total complement of proteins from an organism (i.e., the proteome) prior to and after infection with a virus can show which proteins are down and/or up regulated by the infection. Such an analysis can provide important information about the mechanism by which the virus subverts its host cell, thereby aiding in the development of anti-viral drug strategies. Similarly, comparison of some or all of the proteins of the proteome before and after treatment with a drug can indicate the mechanism of action of the drug, as well as its potential effectiveness and toxicity. As another example, measurement of the state of phosphorylation of protein members of an intracellular cascade involved in turning on and off a given biological process can provide information about the control of the signaling pathway.

A facile method for accurately comparing the levels of proteins and other cellular components and biological materials as a function of time or as the result of particular treatment, such as a hormone, a drug, or a virus, as mentioned above, or an environmental stimulus, such as a temperature change, is needed. It is also necessary to assay these protein levels with high accuracy because small changes in the levels of certain key proteins may, through a complex cascade of molecular events, produce large changes in the biological system.

Two-dimensional electrophoresis has been used to compare proteins from different cell cultures or hosts subjected to differing conditions. See, for example, Anderson, N. G., et al., "Simultaneous Measurement of Hundreds of Liver Proteins: Application in Assessment of Liver Function," *Toxicologic Pathology,* 1996, Vol. 24, No. 1, pp. 72–76; Anderson, N. G., et al., "Twenty years of two-dimensional electrophoresis: Past, present and future," *Electrophoresis,* 1996, Vol. 17, pp. 443–453; Anderson, N. G., "Covalent Protein Modifications and Gene Expression Changes in Rodent Liver Following Administration of Methypyriline: A Study Using Two-Dimensional Electrophoresis," *Fundamental and Applied Toxicology,* 1992, Vol. 18, pp. 570–580; and Anderson, N. G., et al., "Global Approaches to Quantitative Analysis of Gene-Expression Patterns Observed by use of Two-Dimensional Gel Electrophoresis," *Clin. Chem.* 1984, Vol. 30, No.12, pp. 2031–2036.

FIG. 1 is a schematic representation of the processes described in these articles. Proteins from a control cell culture are extracted, purified and separated by one- and two-dimensional electrophoresis. Proteins from another, parallel cell culture, which may include cells exposed to drugs, carcinogens or other such treatments directly or through a host, are also extracted, purified and separated by one- and two-dimensional electrophoresis. FIG. 2 shows exemplary electrophoretic gel samples from each cell culture. Spots at different locations in each gel sample may indicate the presence of different proteins or changes in the proteins in the control versus the treated cells. Spots of different sizes may indicate a change in the quantity of the protein in the treated cells. The gels may be analyzed visually or by labeled maps, bargraphs or numerical tables. See, Anderson, "Twenty years of two-dimensional electrophoresis . . . ", at p. 450. Computer generated arrowplots, which indicate the magnitude and polarity of changes in spots between gel samples of a control and treated cell pool, superimposed on a gel sample of a control cell pool, have also been used. Id. Instead of a control cell sample, the gel sample including the proteins from the treated cells may be compared to a master gel pattern from a library of gel patterns.

Using prior art methods, hundreds of gel samples and hundreds of thousands of protein abundance measurements may be required in a typical study. Id. It is also difficult to maintain the reproducibility of the extraction and purification procedures in each cell sample. Extraction and purification results must be normalized. Precise, accurate and reproducible quantification of the changes between cell pools is also difficult. If a gel spot includes more than one protein, the discrete proteins frequently cannot be identified. Thus, a more practical method of comparing proteins in different cell pools is needed.

Mass spectroscopy is a highly accurate analytical tool for determining molecular weights and identifying chemical structures. Proteins and peptides have been studied by matrix-assisted laser desorption mass spectroscopy and electrospray ionization mass spectroscopy. See, for example, Chait, Brian T. and Kent, Stephen B. H., "Weighing Naked Proteins: Practical, High-Accuracy Mass Measurement of Peptides and Proteins", *Science,* Vol. 257, Sep. 25, 1992, pp. 1885–1894, which is incorporated by reference herein. Matrix-assisted laser desorption time-of-flight mass spectrometers are described in U.S. Pat. Nos. 5,045,694 and 5,453,247, to Beavis, et al., which are assigned to the assignee of the present invention and incorporated by reference herein. Electrospray ionization mass spectrometers are described in U.S. Pat. No. 5,245,186 to Chait et al., and U.S. Pat. No. 4,977,320 to Chowdhury et al., for example, which are also assigned to the assignee of the present invention and incorporated by reference herein. Prior to analysis, the proteins are typically separated by one- or two-dimensional electrophoresis and then digested by an appropriate enzyme. The resulting peptides are then subjected to mass spectroscopy by any of the types of mass spectrometers identified above.

However, quantitative comparisons among proteins within a sample or between samples may be compromised by a number of parameters, such as the ionization efficiency of the mass spectrometer for a particular peptide or protein, the extraction efficiency from electrophoretic gels for a particular peptide and the digestion efficiency of an enzyme at different cleavage sites.

Isotopic labeling by stable or radioactive isotopes has been used to study many aspects of human, animal and plant metabolism. For example, isotopic labeling has been used to study metabolic turnover rates and biosynthesis of proteins and nucleic acids. Microorganisms, organs and tissue extracts, for example, may also be studied through isotopic labeling. The presence of radioactive isotopes in a sample of biological material may be detected by scintillation counters, or autoradiography, for example. However, the use of radioactive isotopes pose hazards to those conducting the experiments and require the use of protective measures, which may be cumbersome and expensive. To avoid this problem, in U.S. Pat. No. 5,366,721, a long-lived radioisotope, such as carbon-14, is administered to a biological host. A reacted fraction is isolated from the host and the radioisotope concentration is measured by mass spectroscopy. See also DeLeecher, A. P. et al., "Applications of isotope dilution—mass spectrometry in clinical chemistry, pharmacokinetics, and toxicology," *Mass Spectroscopy Reviews*, 1992 11, 249–307; Grostic, M. F. et al., "Mass-Spectral Studies Employing Stable Isotopes in Chemistry and Biology," appearing in *Mass Spectroscopy: Techniques and Applications*, edited by Mike, G. W. A., Wily-Interscience (1971), pp. 217–287.

SUMMARY OF THE INVENTION

The present invention is a method for accurately comparing the levels of ionizable components of biological matter, wherein the biological matter differs in some respect from each other, using mass spectroscopy and isotopic labeling.

In one embodiment of the present invention, a method for comparing the relative abundance of a protein of interest in multiple samples of biological matter is disclosed, wherein one of the samples has been modulated by exposure to a treatment, such as a bacteria, virus, drug or hormone, or a stimulus, such as a chemical or environmental stimulus. A first sample of the biological matter is cultured in a first medium containing a natural abundance of isotopes and a second sample of the biological matter is cultured in a second medium containing more or less than the natural abundance of one or more isotopes. One of the samples is modulated, at least portions of the samples are combined and at least one protein is removed from the combined sample.

The removed protein, which may or may not be digested into peptides, is subjected to mass spectroscopy to develop a mass spectrum. The difference in the mass of the isotope in each cell pool results in two distinct, closely spaced peaks for each protein or peptide in the mass spectrum. One peak corresponds to a protein or peptide from a protein from the cell pool with the normal abundance of isotopes. The other peak corresponds to a protein or peptide from the cell pool enriched in one or more of the isotopes. A ratio is computed between the peak intensities of at least one pair of peaks in the mass spectrum. The relative abundance of the protein in each sample may be determined based on the computed ratio. The protein may be identified by the mass-to-charge ratios of the peaks in the mass spectrum, as well as by other means known in the art.

In addition, modifications, such as phosphorylation, glycosylation or acylation, at specific sites on individual proteins may be detected and quantified through mass spectroscopy in accordance with the present invention.

The first sample need not contain a natural abundance of isotopes, as long as at least one isotope in the second sample of biological matter has a different abundance than the abundance of the same isotope in the first sample. Preferably, the isotope which is enriched or depleted is a non-radioactive isotope of nitrogen, oxygen, carbon and/or sulfur. Hydrogen may be used, as well. Radioactive isotopes may also be used.

The effects of two or more modulations can be simultaneously analyzed by preparing additional samples with media containing an isotope with a different abundance than the abundance of the isotope in the other samples, and modulating the additional samples.

Up to the point of the mass spectroscopy, none of the steps of the process discriminates between a protein that contains the natural abundance of isotopes from the same protein from the enriched sample. Thus, the ratios of the original amounts of proteins from the two samples are maintained, normalizing for differences between extraction and separation of the proteins in the samples.

The method is applicable to the components of any type of biological matter which can be ionized and therefore may be analyzed by mass spectroscopy. For example, the component may be a protein, a peptide, a carbohydrate, a lipid, a cofactor and post-synthetic derivatives thereof. The biological matter may be a culture of biological cells, a microbiological culture, biological tissue, an organ, an organism, a collection of organisms, a part of an organism, and a cell-free biological mimetic system, for example.

DETAILED DESCRIPTION OF THE INVENTION

Figure 1:
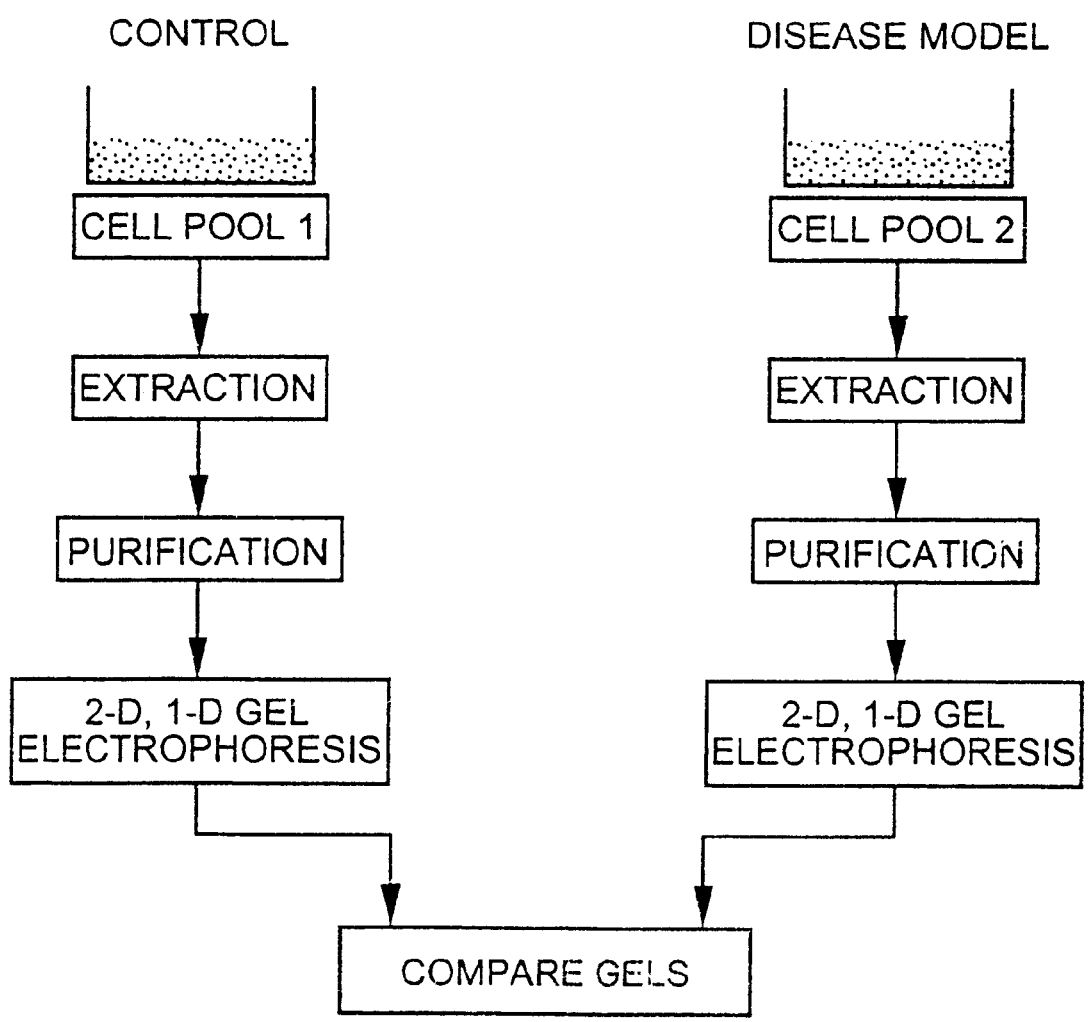
FIG. 1 is a flow chart of a prior art process for comparing proteins from two cell pools, one of which is diseased.
Figure 2:
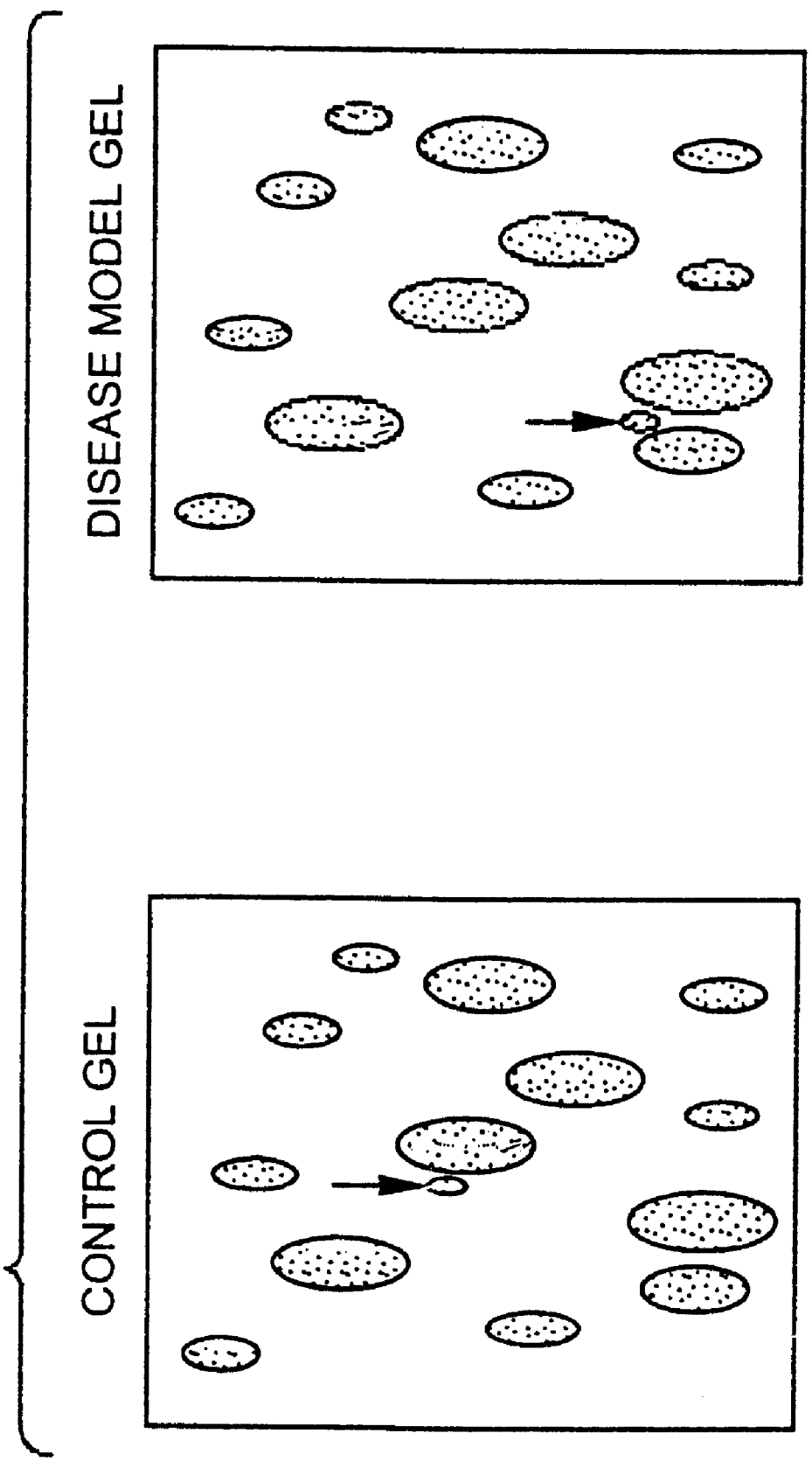
FIG. 2 shows two exemplary electrophoretic gel samples from the process of FIG. 1.
Figure 3:
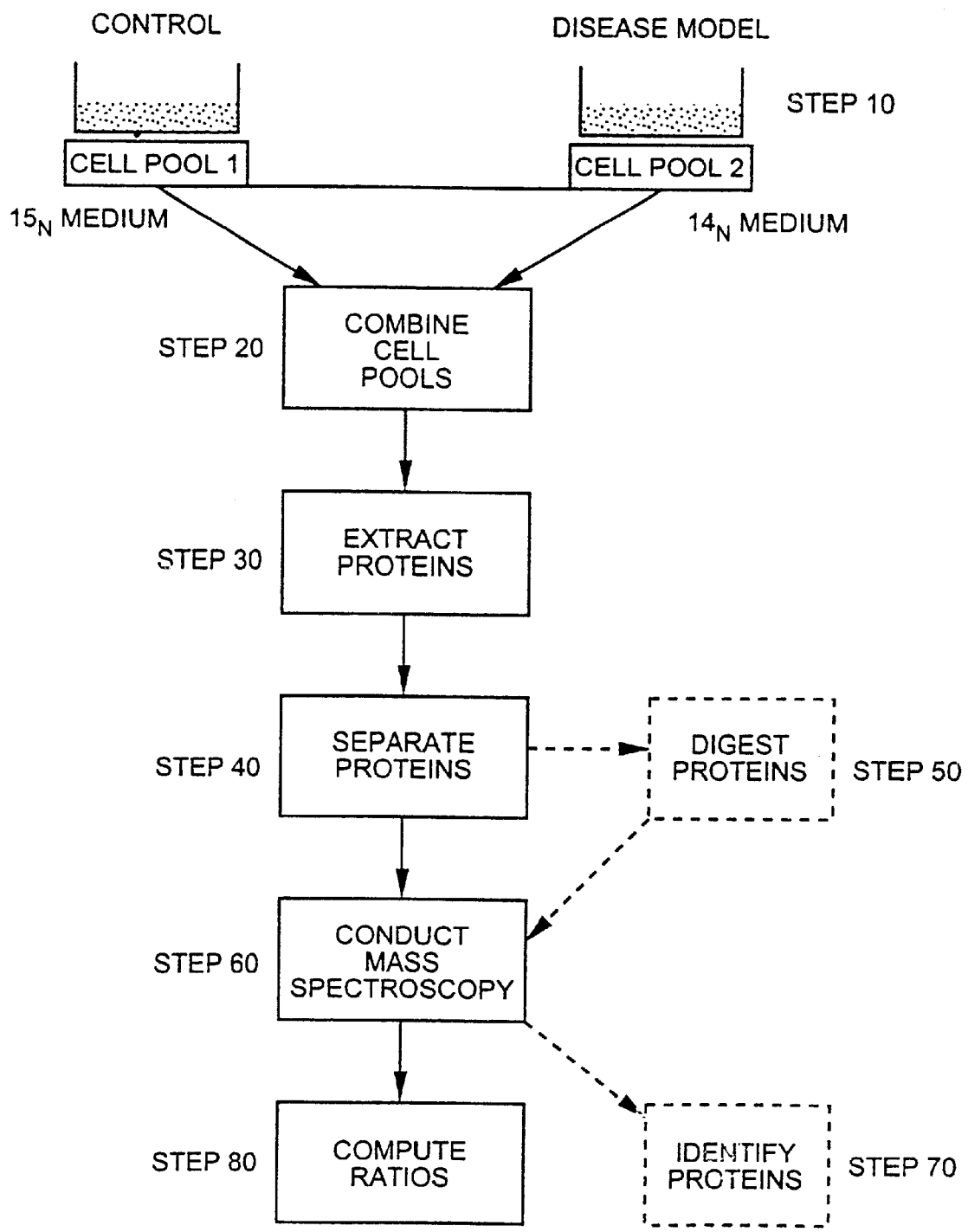
FIG. 3 is a flow chart of one embodiment of the method of the present invention.

FIG. 3 is a flow chart of one embodiment of the process of the present invention for comparing the quantities of proteins in different cell samples. Two cell pools are prepared. (Step 10). One of the cell pools, here Cell Pool 1, contains a cell culture grown or maintained in a medium containing a natural abundance of isotopes. For example, the medium contains 99.6% nitrogen-14 and 0.4% nitrogen-15, which are the naturally occurring abundances of those isotopes of nitrogen. The isotopes of oxygen, carbon, sulfur and other elements are also present in their naturally occurring abundances.

The other cell pool, here Cell Pool 2, contains a cell culture grown or maintained in a medium in which one or more isotopes of nitrogen, carbon, oxygen or sulfur, for example, is not present in a natural abundance. For example, the second medium may be isotopically enriched in one or more of the following isotopes: nitrogen-15, carbon-13, oxygen-17, oxygen-18, and sulfur-34. Enrichment of hydrogen-2 (deuterium) can also be used, however, the enzymatic effects of hydrogen substitution is greater than that of $^{15}N$ and can therefore change the biological process.

High enrichment is preferred. The particular level of enrichment may depend on the isotope chosen. For example, a medium enriched in nitrogen-15 ("$^{15}N$") to between 90%–100% is preferred, with 100% $^{15}N$ enrichment most preferred. Because hydrogen-2 can be toxic, less than 100% hydrogen-2 is preferred. Isotopic depletion may also be used wherein less than the naturally occurring abundance of an isotope is provided in the medium. Non-radioactive isotopes are preferred. Radioactive isotopes may also be used, but are not preferred because of the difficulties the use of such isotopes present, as discussed above.

The first cell pool need not contain a natural abundance of isotopes, as long as at least one isotope in the second cell pool has a different abundance than the abundance of the same isotope in the first cell pool.

It is preferred that the media the cell pools are grown in be identical, except for the presence of the different isotope or isotopes. Bio-Express from Cambridge Isotope Laboratories, Inc., Andover, Mass., is one suitable $^{15}N$ enriched media. Alternatively, the cells may be grown in the same medium and the labeling isotope may be added directly to one culture of cells.

Either of the cell pools, here Cell Pool 2, is modulated by a bacteria, a virus, a chemical, a drug, a hormone, or an environmental change, such as a temperature change, for example. Other treatments or stimulus may be provided, as well. The other cell pool, here Cell Pool 1, acts as a control.

All or portions of the cell pools are then combined. (Step 20). The proteins are extracted from the combined cell pool in a manner known in the art. (Step 30). For example, the cell membranes may be digested or disrupted by standard methods, such as detergents or homogenization in an isotonic sucrose solution. The proteins are then extracted from the combined cell pools by ultra-centrifugation, or other known techniques. For example, antibodies may be used to immunoprecipitate certain proteins or complexes of proteins, as well. The particular method used may be dependent on the particular proteins of interest, as is known in the art.

The mixture of proteins is then separated into the individual proteins or small groups of proteins, also by known techniques, such as one- and/or two-dimensional electrophoresis, ultra-centrifugation, chromatography or affinity binding. (Step 40). Two-dimensional sodium dodecylsulfate-polyacrylamide gel electrophoresis ("SDS-PAGE"), may be used, for example. If an individual protein is extracted from the combined cell pool, such as by use of an antibody, the separation step 40 may not be necessary.

The separated proteins are then preferably digested into peptides. (Step 50). Preferably, the proteins are digested by a proteolytic enzyme. Trypsin is preferred because it cleaves precisely at the sites of lysine and arginine, yielding doubly-charged peptides which typically have a length of from about 5 to 50 amino acids and a molecular weight of between about 700–5,000. Such peptides are particularly appropriate for analysis by mass spectroscopy, especially by electrospray ionization mass spectroscopy. Other site specific proteolytic enzymes which may be used include Ly-C, Asp-N and Glu-C, for example. Pepsin, subtilisin and proteinase 1c are low specificity enzymes which may also be used. Chemical reagents may also be used to digest the proteins. For example, cyanogen bromide may be used to cut a protein into peptides at the site of methionine. BNPS-skatole may be used to cleave at the site of tryptophan. Acid hydrolysis may also be used.

The proteins or digested proteins are then subjected to mass spectroscopy. (Step 60). Any mass spectrometer may be used to analyze the peptides or proteins. For example, the mass spectrometer may be a Matrix-Assisted Laser Desorption/Ionization ("MALDI") Time-of-Flight ("TOF") Mass Spectrometer, available from PerSeptive Biosystems, Framingham, Mass.; an Electrospray Ionization ("ESI") ion trap mass spectrometer, available from Finnigan MAT, San Jose, Calif.; or an ESI quadrupole mass spectrometer, available from Finnigan MAT or the Perkin-Elmer Corporation, Foster City, Calif.

A simple mixture of from 1 to about 5 digested proteins can be analyzed by single-stage mass spectroscopy with any of the mass spectrometers discussed above. Mixtures of greater than six digested proteins are preferably analyzed by a two-stage tandem mass spectroscopy procedure involving collision produced dissociation ("CID"), as is known in the art.

While preferred, the digestion step 50 is not required. One or several whole proteins can also be subjected to mass spectroscopy, avoiding the need for digesting the proteins into peptides, as is known in the art. Single-stage mass spectroscopy may be used to analyze mixtures of large numbers of whole proteins simultaneously.

The protein or proteins subjected to the mass spectroscopy are also preferably identified. (Step 70). The identification step 70 can take place at any time after separation or extraction of a single protein. Protein identification software which uses algorithms to compare the mass spectrum with a database of proteins are available. One such algorithm, ProFound, uses a Bayesian algorithm to search protein or DNA databases to identify the optimum match between the experimental data and the protein in the database. W. Zhang, B. T. Chait, "Proceedings of the 43$^{rd}$ ASMS Conference on Mass Spectroscopy and Allied Topics," Atlanta, Ga. (1995) p. 643. ProFound may be accessed on the World-Wide Web at <prowl.rockefeller.edu> and <www.proteornetrcs.com>. Profound accesses the non-redundant database (NR). Alternative algorithms for protein identification include: Mass Search (cbrg.inf.ethz.ch/subsection3_3.html); MOWSE (www.seqnet.dl.ac.uk//mows.html); MSFIT (prospector.ucsf.edulucsthtml/msfit.htm); Peptide Mass Search (www.mdc-berlin.de/~emu/peptide_mass.html); and Peptide Search (www.mann.embl_heidelberg.de/services/peptidesearch/fr_peptidesearchform.html). See also, James, Peter, "Protein identification in the post-genome era; the rapid rise of proteomics," *Q. Rev. Biophysics.* Vol. 30, No. 4, pp. 279–331 (1997), which is incorporated by reference, herein.

The protein can also be identified by electrophoresis, antibodies Edman sequencing or bioassay, or by other methods conventionally used in the art, after separation of the proteins in step 40.

The ratios of the peak intensities of each pair of peaks are then computed. (Step 80). The ratios give a measure of the relative amount of that peptide in each cell pool, as discussed further, below. The peak intensities are calculated in a conventional manner.

Figure 4:
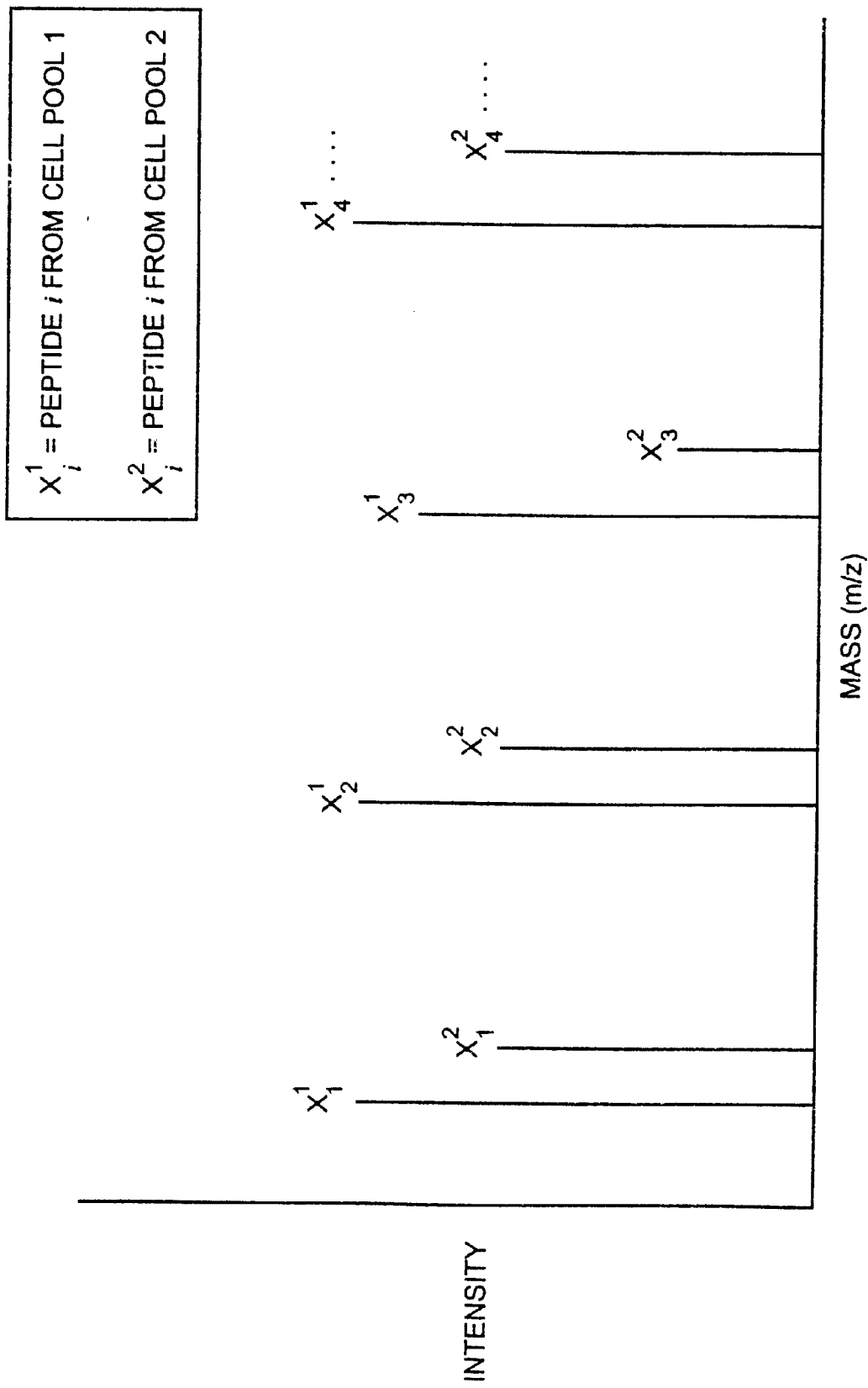
FIG. 4 is an exemplary mass spectrum resulting from a hypothetical experiment conducted in accordance with the method of FIG. 3.

FIG. 4 is an exemplary mass spectrum of four peptides from a single protein resulting from a hypothetical experiment conducted in accordance with the method of FIG. 3.

Because of the difference between the masses of the peptides or proteins and resulting peptides from cells grown in the non-labeled medium and those grown in the labeled, isotopically enriched medium, the results of the mass spectroscopy will generally be a plurality of pairs of closely spaced peaks, each peak being at a different m/z ratio. Since the enriched isotope is typically heavier than the most abundant naturally occurring isotope ($^{15}$N versus $^{14}$N, for example), the peak at the higher m/z ratio is generally indicative of the relative abundance of the peptide from a labeled protein grown in the medium enriched in one or more isotopes. The peak at the lower m/z ratio is generally indicative of the relative abundance of the peptide from an unlabeled protein in the medium containing a normal abundance of isotopes.

Table I, below, lists four ratios of the peak intensities of isotopically labeled peptides of Cell Pool 2 and non-isotopically labeled peptides of the control Cell Pool 1 ($X_i^2/X_i^1$) based on the exemplary mass spectrum of FIG. 4.

TABLE I

| Peptide No. | Intensity Ratio |
|---|---|
| 1 | 0.70 ± .02 |
| 2 | 0.69 ± .02 |
| 3 | 0.30 ± .02 |
| 4 | 0.71 ± .02 |

Since the number of cells in one cell pool may differ from the number of cells in the other cell pool, for any given pair of peaks, the intensity of a peak corresponding to a peptide from one cell pool may differ from the intensity of the peak corresponding to the same peptide from the other cell pool. The ratios between most of the pairs of peaks (which are indicative of peptides derived from proteins unaffected by a given treatment or stimulus), will generally be the same. A deviation from the regularly-observed ratio indicates a difference in the relative quantity of a peptide, and hence a protein, between the two cell pools which may be caused by the modulation to which one of the cell pools has been subjected. The difference can be quantified in accordance with the present invention.

Because the cell pools are combined, other sources of differences in the intensities of the peaks, such as variations in the extraction efficiency of a particular protein from the cell pool, the subsequent extraction efficiency of a protein from the gel, the digestion efficiency of the enzyme used (if any), the ionization efficiency of the mass spectrometer for a particular peptide, and other such factors, affect both cell pools equally. These factors should not, therefore, affect the observed ratios. Analyzing the ratio of the pair of peaks compensates for differences in mass intensities resulting from differences in the ionization efficiency of the mass spectrometer for a particular peptide. Isotopically labeling one of the two cell pools and observing the ratio between the peaks of the isotopically labeled and non-isotopically labeled peptides also compensates for differential effects between the cell pools themselves, such as the presence of a different number of cells in each, providing an internal normalization between the cell samples.

To ensure that the change in the ratios is not caused by the isotopic enrichment itself, the process of FIG. 3 is preferably repeated with the other cell pool being isotopically enriched, i.e., if in the first run the treated cell pool is isotopically enriched, as in FIG. 3, then in the second run, the control cell pool would be isotopically enriched.

The ratios of the intensities of the peaks in the hypothetical spectrum shown in FIG. 4 is about 0.70, except for peptide number 3, whose ratio is about 0.30. This indicates that the relative amount of the protein corresponding to peptide 3 in the treated and control cell pools is different than the relative amounts of the protein or proteins corresponding to peptides 1, 2 and 4. This suggests that the modulation affects the post-translational expression of the protein from which peptide 3 is derived. In an actual example, there would be other pairs of peaks having ratios of about 0.30, corresponding to other peptides from the protein from which peptide number 3 is derived. Analysis of the plurality of peaks having a ratio of about 0.30 would enable an identification of the protein through the protein identification algorithms discussed above.

The percentage difference between the regularly observed ratio of the peak intensities of the peptides from both cell pools and the observed ratio for the modified peptides, e.g., peptide 3, in FIG. 4, is the percentage change in the expression of the protein in the treated cell pool, e.g., Cell Pool 2, which could be caused by the disease or another type of treatment or stimulus. In this example:

$$\frac{0.30 - 0.70}{0.70} \times 100 = -57\%$$

This suggests that the disease decreased the expression of the protein in the modulated Cell Pool 2 by 57%, compared with the expression of the same protein in the control Cell Pool 1. This quantitative change caused by the disease may give insight into the effect of the disease or other such modulation on the cell.

The method of the invention can also be extended to comparing the effects of two or more modulations by preparing three or more cell pools wherein at least one isotope in each cell pool is different. For example, if the proteins in three cell pools are to be compared, preferably one cell pool, which in this example is the non-modulated cell pool, would have a normal abundance of isotopes, the second cell pool would be enriched in $^{15}N$ and the third cell pool would be enriched in a different isotope, such as carbon-13, as well as $^{15}N$. The resulting mass spectrum would then comprise groups of three closely spaced peaks, each corresponding to a protein or peptide from a different cell pool. The ratios between the peak intensities of the proteins or peptides from each of the modulated cell pools and the non-modulated cell pool would be indicative of the relative amount of that peptide in each cell pool.

EXAMPLE 1

To demonstrate the internal normalization provided by mixing isotopically enriched and non-enriched proteins, the following experiment was conducted. No modulation was applied to either cell pool in this example.

Human Abelson protein tyrosine kinase Src homology domain-2 (Abl-SH2) was derived from *E. coli* DHα5 strain cells grown in minimal medium M9, with 1 gram per liter of $^{15}NH_4$ Cl (ammonium chloride including $^{15}N$) as the sole source of $^{15}N$. The preparation of labeled and unlabeled Abl-SH2 from *E. coli* DHα5 is described in Gosser, Y. Q., et al., *Structure* 3, 1075 (1995), which is incorporated by reference, herein. The following samples were prepared:

TABLE II

| | Sample Number | | | | | | |
|---|---|---|---|---|---|---|---|
| | 1 | 2 | 3 | 4 | 5 | 6 | 7 |
| Natural Protein (A) picomole/microliters | 0.1 | 0.25 | 0.5 | 1.0 | 1.5 | 2.0 | 2.5 |
| $^{15}N$ Labeled Protein (B) picomole/microliters | 1.5 | 1.5 | 1.5 | 1.5 | 1.5 | 1.5 | 1.5 |

The natural samples were prepared by dilution into 50 mM ammonium carbonate ($NH_4HCO_3$). 10 microliters of the natural and labeled proteins were combined and subjected to SDS-PAGE with 4–20% acrylamide concentration tris-glycine gel, available from Novex, San Diego, Calif., in the form of pre-cast mini-gels. A voltage of 130 volts was applied for two hours. After two hours, the gel was stained with Copper Stain from Bio-Rad Laboratories, Hercules, Calif.

Each protein spot or band was cut out of the gel and destained twice, for 10 minutes each. The gel pieces were then washed twice, for 15 minutes each. The gel pieces were then crushed.

0.2 micrograms of trypsin, from Boehringer Mannheim, and 50 millimolar $NH_4 HCO_3$ (ammonium carbonate) having a pH of 8 were added to the crushed gel pieces. The mixture was allowed to stand for 2 hours at 37° C. The peptides were then removed from the gel pieces by acetonitrile ($CH_3CN$) at a concentration of 75%.

The solution was dried in a SpeedVac, available from Savant, Holbrook, N.Y. The lyophilized material was then dissolved in 7 microliters of about 50% $CH_3CN$, about 50% $H_2O$ and about 0.1% trifluoroacetic acid ("TFA"). 10% of the sample solution, 0.7 microliters, was mixed with 0.7 microliters of 2–5 dihydroxybenzoic acid (gentisic acid) referred to as MALDI-MATRIX DHB, at a concentration of 60 grams per liter. MALDI-MATRIX DHB is available from Aldrich Chemical Company, Inc., Milwaukee, Wis. The solution was then analyzed with a Model STR Matrix-Assisted Laser Desorption/Ionization time-of-flight mass spectrometer ("MALDI-TOF-MS"), available from PerSeptive Biosystems.

Figure 5:
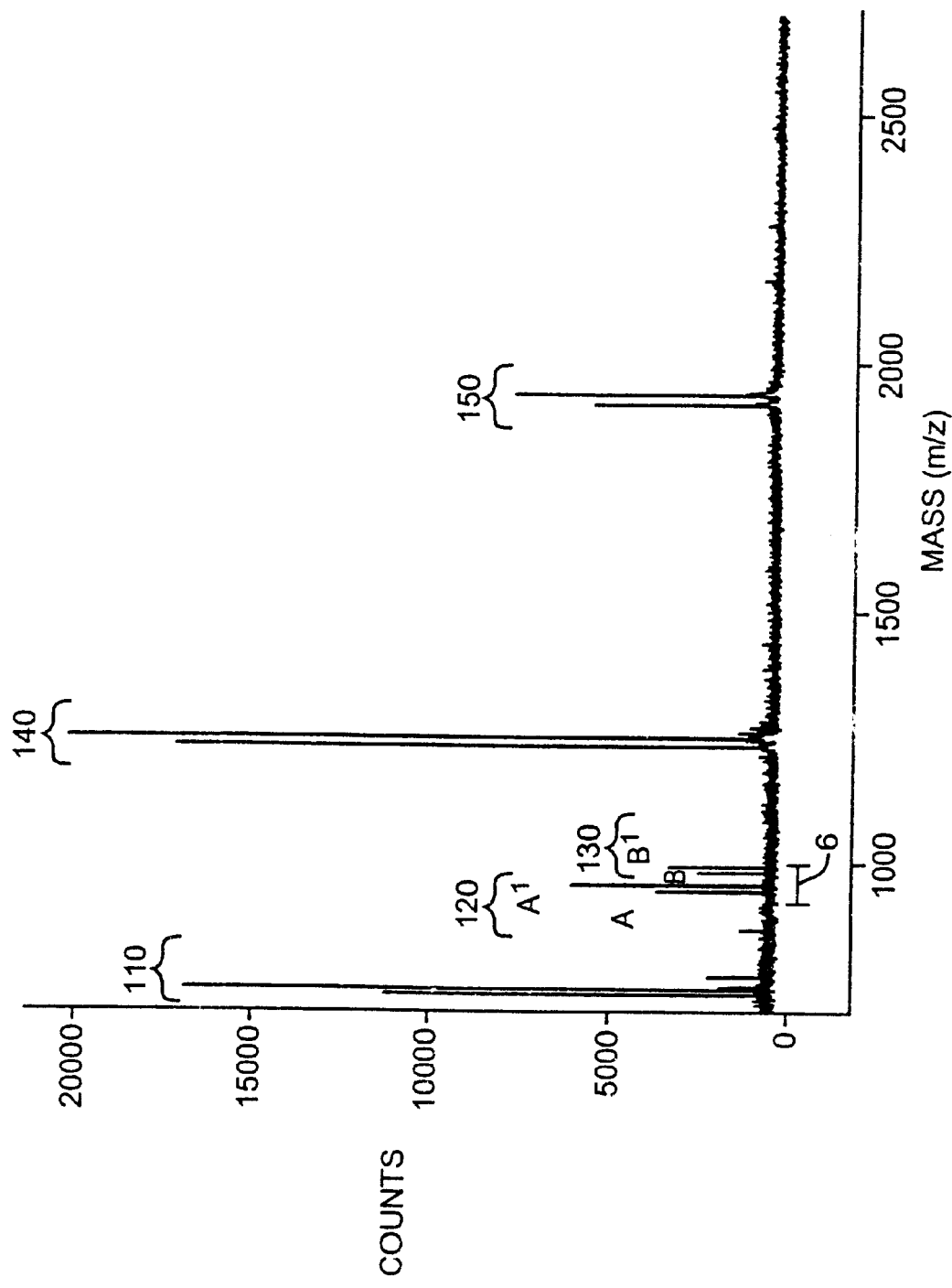
FIG. 5 is a portion of a mass spectrum of Abl-SH2.
Figure 6:
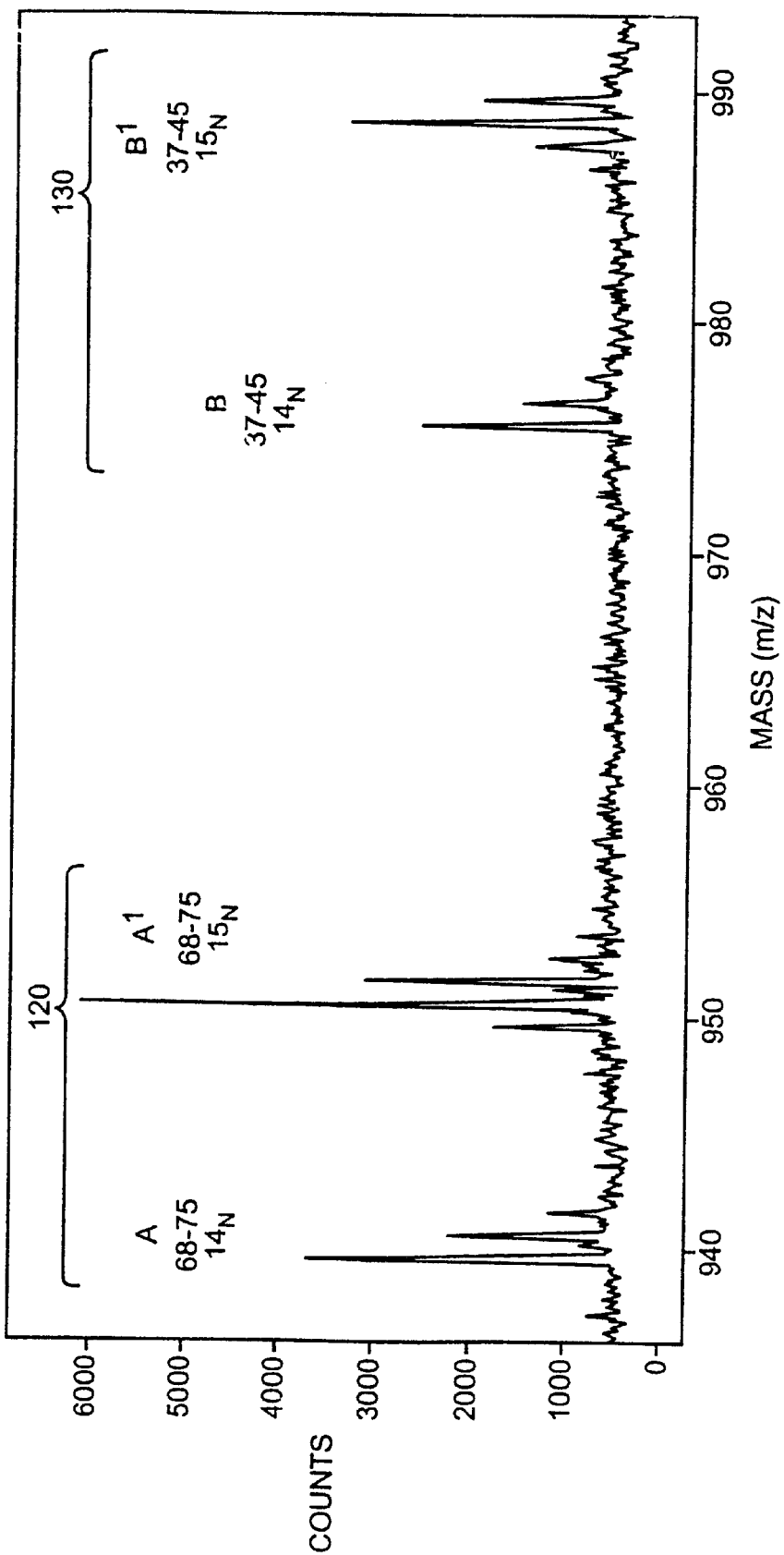
FIG. 6 is an enlarged view of the region 6 of the mass spectrum of FIG. 5.

A portion of the resulting mass spectrum is shown in FIG. 5. Several pairs of peaks 110, 120, 130, 140 and 150 are shown. In each pair, the peak of the higher mass-to-charge ratio ("m/z") is indicative of a peptide of Abl-SH2 from the cell pool enriched with $^{15}N$, while the peak at the lower m/z ratio is indicative of a peptide of the Abl-SH2 from the non-enriched cell pool, which is predominantly $^{14}N$. For example, in peak pair 120, peak A is indicative of a peptide from the unlabeled cell pool while peak A' is indicative of the same peptide from the labeled cell pool. FIG. 6 is an enlarged view of the region 6 of the mass spectrum of FIG. 5, including the peaks 120 and 130 in the mass-to-charge ratio (m/z) range of about 940–990. The corresponding peaks from FIG. 5 are similarly labeled in FIG. 6. The closely bunched multiple peaks in FIG. 6 are due to the naturally occurring distribution of the various isotopes of nitrogen, carbon, oxygen, sulfur and hydrogen in the peptides.

The amino acid sequence of Abl-SH2 appears below:

```
            1         10        20        30        40        50
  1 GSGNSLEKHSWYHGPVSRNAAEYLLSSGINGSFLVRESESSPGQRSISR    [SEQ. ID NO:1]

51 YEGRVYHYRINTASDGKLYVSSESRFNTLAELVHHHSTVADGLITTLHYP

101 APKRGIHRD
```

The pair of peaks 110 m/z~737 in FIG. 5 corresponds to the peptide sequence starting with the amino acid number 55 and ending with 59; the pair of peaks 120 at m/z~940 corresponds to the peptide sequence spanning amino acid numbers 68–75; the pair of peaks 130 at m/z~976 corresponds to the peptide sequence spanning amino acid numbers 37–45; the pair of peaks 140 at m/z~1225 corresponds to the peptide sequence spanning amino acid numbers 9–18; and the pair of peaks 150 at m/z~1910 corresponds to the peptide sequence spanning amino acid numbers 19–36.

The average peak intensity ratio and relative standard deviation ("RSD") for each of 5 peptides from the digested Abl-SH2 in 7 individual mass spectral measurements are shown below:

TABLE III

Peak Intensity Ratio
Theoretical Loading Amount of $^{14}$N protein −1 picomole ("pm")
($^{15}$N protein amount - 1.5 pm)

| Peptide | m/z (M + H) | Peptide Sequence | Average Ratio (n = 7) | R.S.D. |
|---|---|---|---|---|
| 1 | 737 | 55–59 | 0.61 | 6.9% |
| 2 | 940 | 68–75 | 0.60 | 5.6% |
| 3 | 976 | 37–45 | 0.67 | 13.6% |
| 4 | 1225 | 9–18 | 0.62 | 3.1% |
| 5 | 1910 | 19–36 | 0.61 | 6.0% |
| 5 peptides total | | | 0.62 | 4.8% |

The average of the RSD for the seven spectral measurements of the five peptides was 4.8%.

Figure 7:
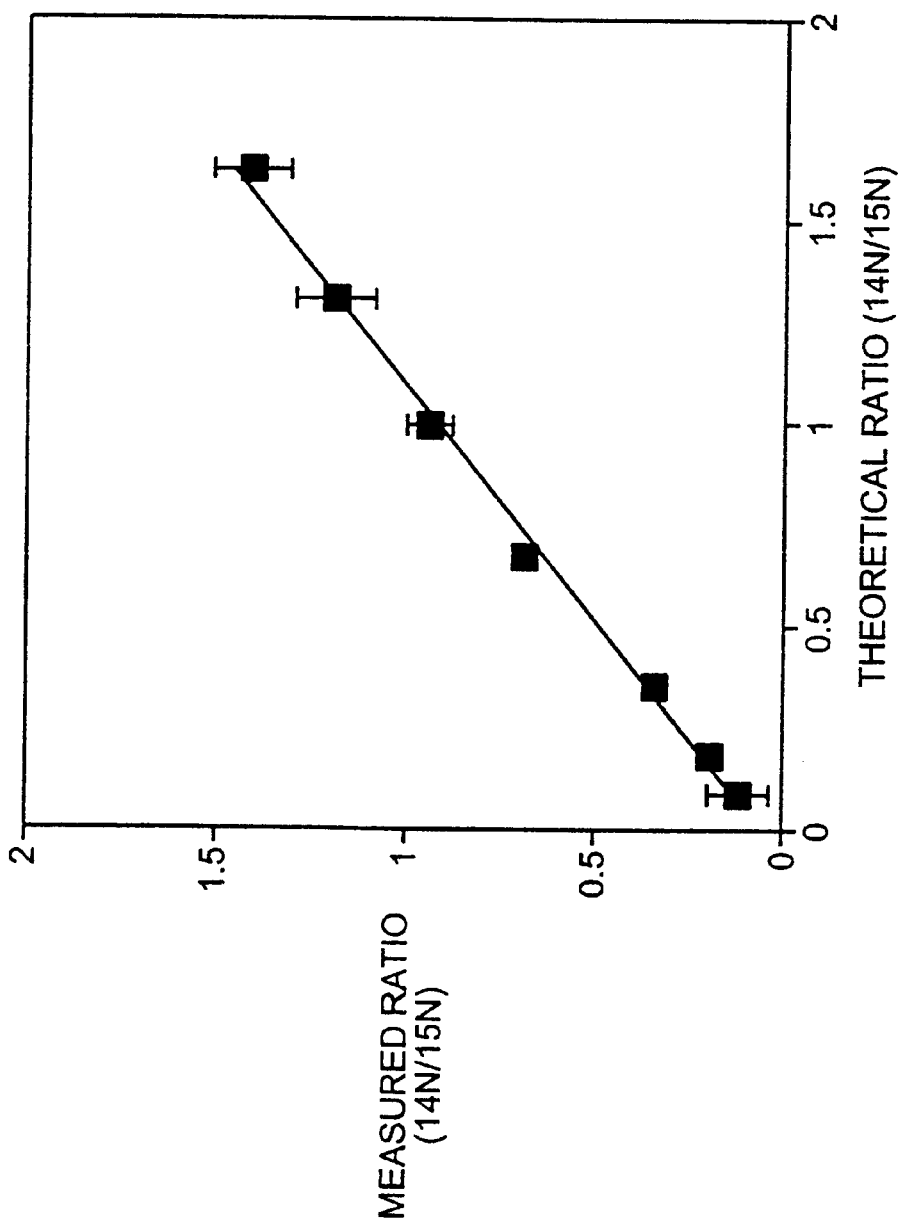
FIG. 7 is a graph of measured ratios between the peak intensities corresponding to peptides of Abl-SH2 from an unlabeled (nitrogen-14) sample and the peak intensities corresponding to a labeled (nitrogen-15) sample, versus the expected ratios, based on seven spectral measurements of each of the samples of Table II.

FIG. 7 is a graph of the measured ratios between the peak intensity corresponding to unlabeled $^{14}$N and the peak intensity corresponding to labeled $^{15}$N, based on seven spectral measurements of each of the samples of Table II, above. Since no modification was applied to either cell pool, the only difference between the samples in this example was the concentration of the natural protein in each cell pool. The value of the intensity ratios of each of the pairs of peaks for each peptide should therefore be equal to the ratio of the concentrations of the protein Abl-SH2 in each cell pool. The intensity ratio was found to be linear (R=0.997) over an abundance ratio of more than 10:1.

EXAMPLE 2

In another example, the levels of high abundance proteins derived from two pools of *Saccharomyces* ("*S.*") *cerevisiae* cells that differed only in their ability to express the G1 cyclin CLN2 was analyzed. CLN2 is important in regulating the G1-S transition in budding yeast, but the effect of its expression on the levels of specific proteins and their modification is largely unknown. See F. R. Cross, *Curr. Opin. Cell Biol.* 6, 790 (1995). The cells in one cell pool were cln1 cln2, mutant yeast harboring a GAL1::CLN2 overexpression cassette. The cells in the second cell pool were yeast without the overexpression cassette. Both populations were proliferating but only one population was expressing CLN2. The expressing population is designated "CLN2$^+$". The non-expressing population is designated "cln2$^-$."

A first combined sample contained 1 ml of unlabeled ($^{14}$N) extract of cln2$^-$ plus 1 ml of $^{15}$N-labeled extract of CLN2$^+$. A second combined sample contained 1 ml of unlabeled ($^{14}$N) extract of CLN2$^+$ plus 1 ml of $^{15}$N-labeled extract of cln2$^-$. These two different samples were prepared to control for systemic errors in the measurements.

The enriched media was Bio-Express-1000 (discussed above), specified by the manufacturer as enriched to greater than 96% $^{15}$N. The enriched and non-enriched media were both glucose-free and were supplemented with unlabeled tryptophan. Galactose was added to each media to 0.3%. The cells were grown overnight to mid-log phase (OD≦1.0) at 30° C. with shaking.

The combined samples were separated by a combination of reversed phase high performance liquid chromatography ("HPLC") and SDS-PAGE. The HPLC column was 10 mm×100 mm, and contained C4 silica gel (Brownlee Prep-10 Butyl, 20 μm, 300 Å, Perkin Elmer, Norwalk, Conn.). The HPLC mobile phase A was composed of 67% ACS grade formic acid and 33% water. The mobile phase B was composed of 67% formic acid and 33% acetonitrile. The flow-rate was 1 ml/min. The gradient curve was 0–5 min B conc. 0%; 5 min–10 min B conc. from 0–30%; 10 min–110 min B conc. from 30–100%; 110 min–120 min B conc. was 100%.

A total of 57 fractions of 2 ml each were collected. The HPLC injection volume was 14 ml, composed of 2 ml of whole yeast extract and 12 ml of mobile phase A.

After HPLC, the proteins were precipitated from each 2 ml fraction by adding 10 ml of water, 1 ml of 0.4% deoxycholate and 1 ml trichloroacetic acid (1 g/ml). The solution was maintained at 4° C. for 1 hr and then centrifuged at 2,200× g for 30 min at 4° C. The supernatant was then discarded. One milliliter of 80% acetone was added and the sample was transferred to a new Eppendorf tube. This sample was maintained at −20° C. for 1 hr before centrifuging at 14,000× g for 5 min at room temperature. The supernatant was discarded and aqueous NaOH was added for neutralization.

SDS-PAGE sample buffer was added and each fraction was run on a separate lane of an 8–16% gradient tris-glycine gel at constant voltage of 110 V. The gels were stained with colloidal Coomassie Brilliant Blue. The gradient tris-glycine gel and Coomassie Brilliant Blue are available from Novex, for example.

The protein bands were excised from the gels with a scalpel and placed into Eppendorf tubes. The gel pieces were destained and washed until clear with methanol/water/acetic acid 5:4:1 (v/v/v) with 3× exchange of solution, followed by a 30 min vortex in high purity water. The water was discarded and the gel sliced into 2–3 mm pieces, soaked in 0.5 ml of acetonitrile, and vortexed.

After the gel pieces had shrunk and turned opaque, the acetonitrile was discarded. A trypsin solution of 0.2 micrograms ("μg") in 50 mM NH$_3$HCO$_3$ was added in sufficient volume, 20–50 microliters ("μl"), to re-hydrate the gel pieces. After incubation for 2 hours at 37° C., 30 μl of acetonitrile was added to the gel pieces and vortexed for a few minutes. A further 30 μl of acetonitrile was added and the process repeated until the gel turned opaque white. The supernatant was transferred to a new tube, the gel was rehydrated with water (30 μl) and the extraction steps repeated. The supernatant was dried using a SpeedVac and each dried sample was re-dissolved in 5 μl of acetonitrile/ 0.1% aqueous trifluoroacetic acid ("TFA") 1:2 (v/v). 0.5 μl of this sample solution was loaded onto the sample plate together with 0.5 μl of matrix solution (DHB: 2,5-dihydroxybenzoic acid). Mass spectrum measurements were obtained using a MALDI-TOF-MS Model STR, from PerSeptive Biosystems, Framingham, Mass., operated in reflector mode.

Figure 8:
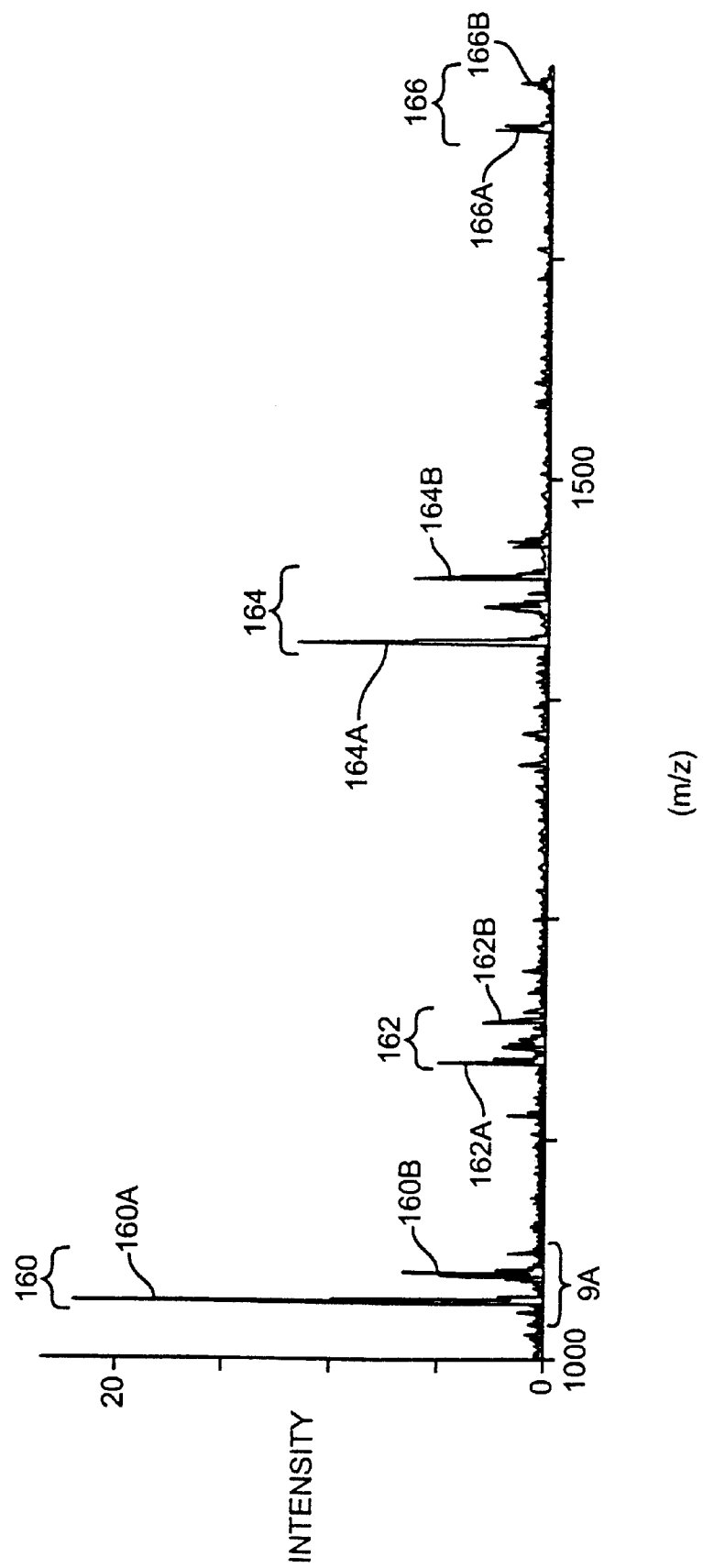
FIG. 8 is a portion of a mass spectrum of the peptide of the protein elongation factor 1-α from a combined pool of labeled and unlabeled *Saccharomyces cerevisiae* which differed only in their ability to express the cyclin CLN2.
Figure 10:
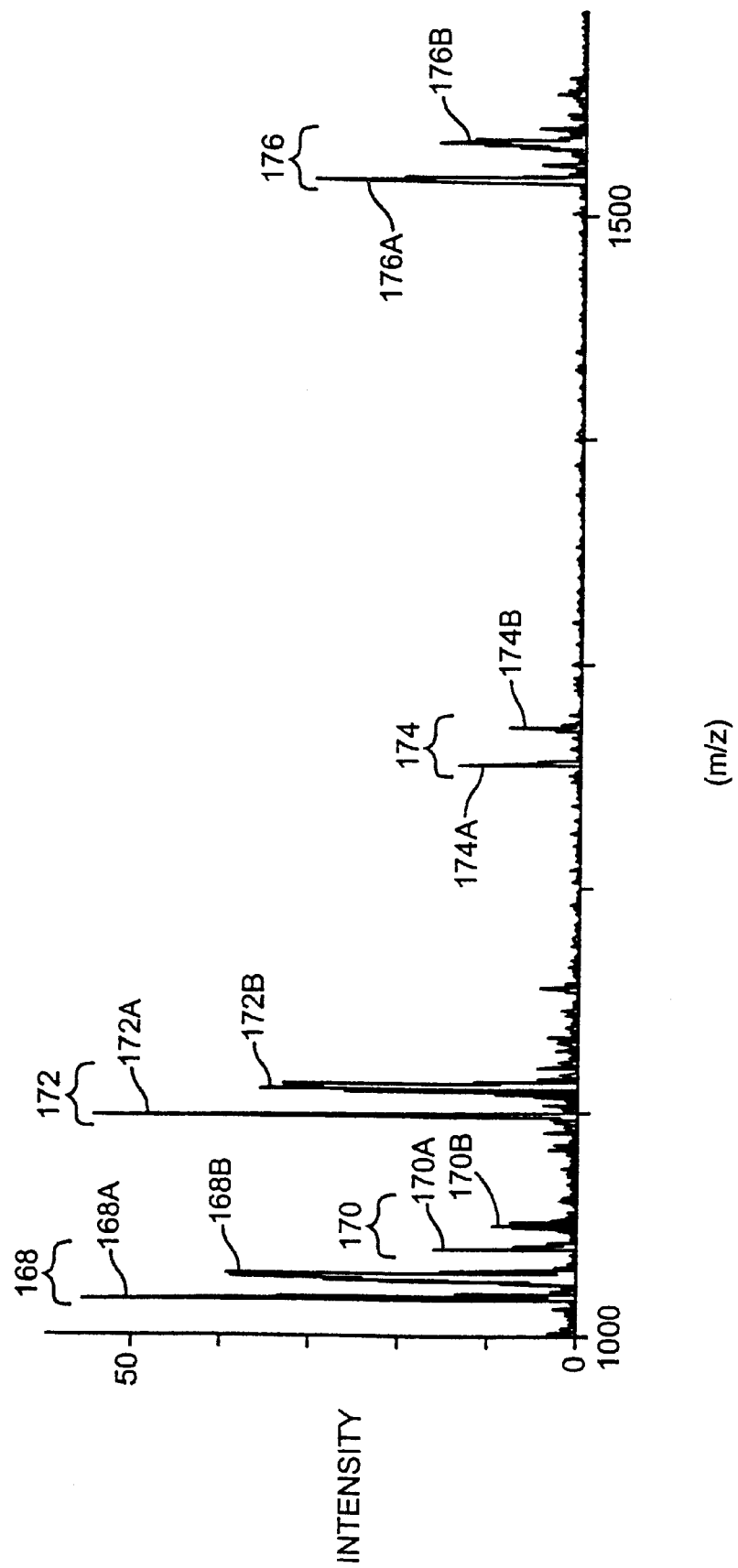
FIG. 10 is a portion of a mass spectrum of the peptides of the protein triosephosphate isomerase from the combined cell pool described above with respect to FIG. 8.

The abundances of a selection of individual proteins from the two samples were then compared. FIGS. 8 and 10 are examples of MALDI-TOF-MS mass spectra of tryptic peptides from the combined cell pools of unlabeled $^{14}$N cln2$^-$ and labeled CLN2$^+$. The peptides in the mass spectrum of FIG. 8 originate from one single protein while the peptides in the mass spectrum of FIG. 10 originate from another single protein. These proteins were isolated from several hundred separated by the combination of reversed-phase HPLC and SDS-PAGE, as described above. FIG. 8 shows pairs of peptide peaks 160, 162, 164 and 166. FIG. 10 shows pairs of peptide peaks 168, 170, 172, 174 and 176. Peaks 160a, 162a, 164a and 166a in FIG. 8 and peaks 168a, 170a, 172a, 174a and 176a in FIG. 10 arise from the unlabeled ($^{14}$N) cln2$^-$ protein. Peaks 160b, 162b, 164b, 166b in FIG.

8 and peaks 168b, 170b, 172b, 174b and 176b in FIG. 10 arise from $^{15}$N labeled CLN2+ protein.

Figure 9B:
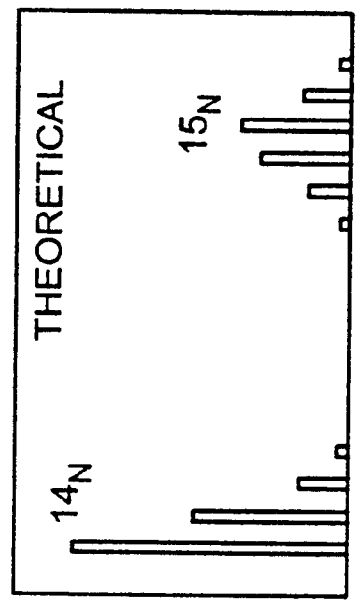
FIG. 9b shows the theoretical isotope distributions of nitrogen-14 and nitrogen-15.
Figure 9A:
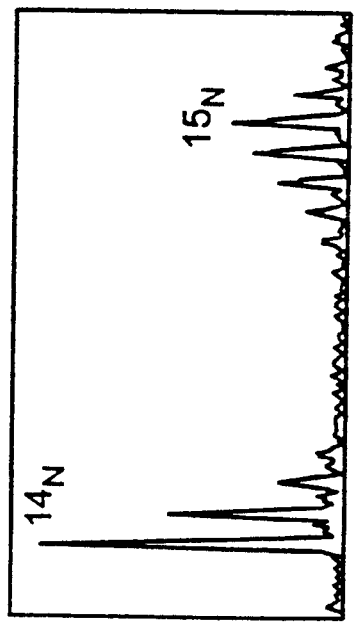
FIG. 9a is an enlarged view of region 9a in the mass spectrum of FIG. 8, showing a pair of peaks from a single peptide.

FIG. 9a is an enlarged view of one pair of peaks 160 in region 9a of the mass spectrum of FIG. 8. The cluster of peaks 160a corresponds to isotopically resolved components of the unlabeled peptide while the cluster 160b corresponds to the isotopic components of the $^{15}$N labeled peptide. FIG. 9b shows the theoretical isotope distribution of $^{14}$N (160a') and $^{15}$N (160b'). Tests of the goodness of fit of the theoretical isotope distribution (FIG. 9b) to the experimental distribution (FIG. 9a) revealed that the level of incorporated $^{15}$N was 93±1%. The multiple pairs of peaks within a spectrum provide multiple measurements of the relative abundance for each identified protein. For each protein subjected to mass spectroscopy, the ratio of the abundance of the protein in the two cell pools was obtained from the intensity ratios of the pairs of peaks in the corresponding spectrum of tryptic peptides by comparing the sum of the intensities of the isotopically resolved components of the unlabeled peptide with the corresponding sum from the $^{15}$N labeled peptide.

The sets of masses of the lower mass components of each pair (i.e., sets of tryptic peptides from the unlabeled proteins) were used to identify the proteins from the *S. cerevisiae* database with the protein identification algorithm ProFound, discussed above. The spectrum of FIG. 8 was found to originate from the protein "elongation factor 1-α" ("EF1-α") while the spectrum of FIG. 10 was found to originate from the protein "triosephosphate isomerase" ("TIM"). The ProFound probability value ("P") for EF1-α was 1.00, readily discriminating against the second ranked choice of clb5 (p=9.0$^{-20}$). The ProFound probability score for TIM was 1.00, while the second ranked choice was ORF YDL100c (P=1.0$^{-16}$).

The relative abundance of a selection of proteins in the cln2− versus CLN2+ cell pools determined from the ratio of labeled ($^{15}$N) versus unlabeled ($^{14}$N) peptide mass spectrometric peak intensities is shown in Table IV, below. Measurement of 42 high abundance yeast proteins revealed that these ratios fall into two categories. The first category, which includes the majority of the proteins studied, yielded intensity ratios that are the same to within the relative experimental error (±10%) of the measurement. The average of this category of intensity ratios were normalized to 1.00 on the assumption that they arise from proteins whose relative abundances do not change in the two cell pools. Elongation factor 1-α falls into this first category. The second category arises from proteins whose relative abundance differs in a statistically significant manner (Standard Deviation>3) from the first category. Triosephosphate isomerase falls into this second category because its unlabeled-to-labeled peak ratio was determined to be 0.58. Only two other proteins of the 42 sampled, a putative peroxisomal membrane protein, ORF YLR109w (4) (ratio 0.67) and S-adenosylmethionine synthetase 2 (Sam2) (ratio 0.70), were observed to fall in this second category.

TABLE III

| Molecular Mass (kDa) | | | | cln2− ($^{14}$N) | cln2− ($^{15}$N) |
|---|---|---|---|---|---|
| Meas | Calc | Gene | Protein Name | CLN2+($^{15}$N) | CLN2+($^{14}$N) |
| 23 | 21.6 | tsa1 | Thiol-specific antioxidant protein | 0.89 | 0.80 |
| 27 | 26.7 | tpi1 | Triosephosphate isomerase | 0.58 | 0.59 |
| 29 | 27.5 | gmp1 | Phosphoglycerate mutase 1 | 1.08 | 1.14 |
| 34 | 34.8 | bel1 | Guanine nucleotide binding protein | 1.10 | 1.08 |
| 37 | 35.6 | tdh3 | Glyceraldehyde 3-phosphate dehydrogenase 3 | 1.12 | 1.04 |
| 45 | 44.7 | pgk1 | Phosphoglycerate kinase | 0.98 | 1.09 |
| 49 | 46.7 | eno2 | 2-phosphoglycerate dehydratase | 0.98 | 0.94 |
| 51 | 49.9 | tef1 | Elongation factor 1-α | 1.00 | 0.84 |
| 60 | 54.5 | cdc19 | Pyruvate kinase 1 | 1.12 | 0.97 |
| 90 | 93.3 | eft1 | Elongation factor 2 | 0.91 | 1.00 |
| 110 | 111 | kgd1 | α-ketoglutarate dehydrogenase | 0.96 | 1.11 |
| 120 | 116 | yef3 | Elongation factor 3 | 0.86 | 1.00 |

In Table III, Column 1 "Meas" is the molecular mass of the peptide as determined by SDS-PAGE, Column 2 "Calc" is the calculated molecular mass and Column 3 "Gene" is the Yeast Protein Database (4) gene name.

The normalized intensity ratios from the cln2− ($^{15}$N)/CLN2+ ($^{14}$N) (Column 6) cell pools were found to be in agreement with those from cln2− ($^{14}$N)/CLN2+ ($^{15}$N) (Column 5) pools to within the statistical uncertainty of the measurement, as shown in Table III, above.

Additional examples of proteins by Yeast Protein Database gene name that were identified from the two cell pools together with their abundance ratios cln2− ($^{14}$N)/CLN2+ ($^{15}$N) in parentheses are: ilv5 (0.93); grs1 (0.97); acs2 (0.99); por1 (1.06); pfk2; cdc48; gdh1; pfk2 (0.95); cdc48 (0.90); gdh1 (1.06); pet9 (1.09); pdc1 (1.00); YLR109w (0.67); fba1 (1.18); asn2 (0.97); cys4 (1.05); idh1 (1.10); rpl5 (0.99); efb1 (0.96); YKL056c (1.14); tif51a (0.94); rps5 (1.16); act1 (1.12); hxk2 (1.11); pgi1 (1.19); ssa1 (0.95); fas1 (0.99); hsc82 (0.84); hom6 (0.96); rpp0 (1.03); rnr2 (0.91); bmh1 (0.91); sam2 (0.70).

Through the process of the present invention, it was demonstrated that the abundance of the triosephosphate isomerase, ORF YLR109w and S-adenosylmethionine synthetase 2 (Sam2) was less in the cln2− sample than in the CLN2+ sample, while the abundance of the elongation factor 1-α was the same in both samples. The biological implications of the change in the abundances of these proteins remain to be elucidated.

Based on a statistical analysis of the results, it is believed that changes in the abundance of proteins outside of two standard deviations (>20%) can be readily discerned.

The method of the present invention can also be applied to the detection of changes in the levels of protein components of incompletely separated mixtures provided that individual peptides in the MALDI-MS peptide map can be unambiguously assigned to specific proteins. Thus, for example, two 75 kDa proteins, glycyl-tRNA synthetase and acetyl coenzyme A synthetase 2, were identified by the algorithm ProFound, discussed above, which also automatically identifies proteins present as binary mixtures, and their abundance changes determined from a single gel band. These same identifications were made by subjecting a portion of the same sample from the 75 kDa band to HPLC separation followed by online electrospray ionization mass spectrometry ("ESI-MS") and ESI-tandem mass spectroscopy analysis using an ion trap mass spectrometer. D. Ashcroft et al., *Electrophoresis* 19, 968 (1998). The tandem mass spectroscopy ("MS/MS") experiment identified proteins from the fragmentation patterns of individual peptides using the search algorithm PepFrag, which can also be accessed on the World-Wide Web at the same cite as ProFound, identified above. The corresponding MS experiment was used to obtain the intensity ratio for quantification. This combined liquid chromatography mass spectroscopy ("LC-MS") and liquid chromatography tandem mass spectroscopy ("LC-MS/MS") approach should also allow for the quantitative analysis of even more complex mixtures of proteins.

Site Specific Modifications

The method of the present invention also enables the identification of the site (peptide) of a modification or modifications of a protein and quantification of the difference in the degree of the modification of the protein in the control and treated cell pools, which may give insight into the mechanism of a disease or other cellular process. A hypothetical example is discussed below.

A control cell pool and an isotopically labeled, diseased cell pool are prepared and combined and the proteins extracted and separated, as described above. A single protein of interest is removed from the gel, digested and subjected to mass spectroscopy, also as described above. FIG. 4 and Table I demonstrate exemplary results for this example, as well.

Peptides from the two cell pools that either remain unmodified or do not undergo a change in the level of modification yield pairs of peaks with a fixed ratio of intensities—a ratio that can be used to normalize the amounts of the protein from the two cell pools. By contrast, peptides that undergo a change in their level of modification yield pairs of peaks with intensity ratios that reflect these changes.

In FIG. 4, the ratios between the intensities of each pair of peaks corresponding to the same peptide from each cell pool is substantially the same, except for peptide 3. This deviation from the norm could be indicative of a change in the peptide in the corresponding protein in the diseased cell pool, which could give insight into the mechanism of the disease. For example, such a deviation could be indicative of greater or less phosphorylation, glycosylation, acylation, etc. of that peptide in the diseased cell pool than in the normal cell pool.

The m/z values of the pair of peaks in the mass spectrum is indicative of the type of change in the peptide, i.e., whether a phosphate, carbohydrate or other such group is bonded to the peptide or not.

Two cases are considered. In the first case, the m/z ratio indicates that no modification of the peptide has taken place, for example, the peptide has not been phosphorylated. In the second case, the m/z ratio indicates that the peptide has been modified, such as by being phosphorylated. The percent difference between the regularly observed ratio and the observed ratio for peptide 3 in the second case is the change in the percentage of those peptides in the diseased cell pool which have been modified compared with the percentage of those peptides which have been modified in the control cell pool, here:

$$\frac{0.30 - 0.70}{0.70} \times 100 = -57\%$$

In this example, fifty seven percent of the peptide 3 which was present in the control cell pool has been modified in the diseased cell pool. Hence, 43% of the peptide 3 which was present in the control cell pool has not been modified in the diseased cell pool.

Conclusions can also be drawn as to the level of the state of modification, as shown in Example 3, below.

EXAMPLE 3

In this example, the degree of phosphorylation of PAK-related Sterol 20 protein kinase ("STE 20") in normal and mutant yeast cells during a signaling cascade were compared.

Cln2–Cdc28 cyclin-dependent kinase inhibits the mating factor signal transduction pathway by interfering with the function of Ste20, which correlates with Cln2-dependent in vivo phosphorylation of Ste20. See, for example, Oehlen, L. J. W. M., Cross, F. R., *Genes Dev.* 8, 1058 (1994); Oehlen, L. J. W. M., Cross, F. R., *J. Biol. Chem.* 273, 25089 (1998); Wu C, Leeuw T, Leberer E, Thomas D Y, Whiteway M., *J. Biol. Chem.* 273, 28107 (1998). The differences in phosphorylation of $Ste20_{trunc}$ in CLN2+ versus cln2- cell pools were monitored in accordance with the method of the present invention to identify Cln2–dependent in vivo phosphorylation sites in Ste20.

Plasmid pYGEX-STE20 (B3553) expresses GST-Ste20 from the GAL1 promoter, as described in R. L. Roberts, et al., *Cell* 89, 1055–65 (1997). GST-Ste20 phosphorylation site mutants were amplified via PCR from pVTU-STE 20-based constructs using an internal oligonucleotide upstream of the BamHI site and a 3' oligo which hybridized outside of the multiple cloning site of the plasmid. The 3' oligo added an SpeI site, and PCR products were cleaved with BamHI and SpeI and transferred to B3553 cut with BamHI and XbaI to create wild type and mutant STE20 alleles.

To prepare the $GST-Ste20_{trunc}$ fusion proteins for mass spectroscopy, $GST-Ste20_{trunc}$ fusion proteins spanning residues of 496–939 of full-length Ste20 for mass spectrometer analysis were made by transforming cells (strain BOY491 (cln2-) or BOY493 (CLN2+)) with a plasmid expressing GAL1p::GST-Ste20. The cells were grown in SCGal-Ura overnight, to an optical density between 0.8 and 1.0. The cells were pelleted, washed in wash buffer of 50 mM Tris-HCl pH 7.5, 100 mM NaCl, 5 mM EDTA, and broken with glass beads in 50 mM Tris-HCl pH 7.5, 250 mM NaCl, 5 mM EDTA, 0.08% Triton-X-100, plus protease inhibitors ("TNET"). Clarified extract was incubated with glutathione agarose for 1 hr at 4° C. with rotation. The agarose was pelleted, washed 3 times with TNET and the protein was eluted either with an equal volume of 2× SDS-PAGE sample buffer or with 5 mM glutathione prepared in 50 mM Tris-HCl pH 8.0. Samples eluted with glutathione were concentrated using Microcon-30 microconcentrators available from Millipore Corporation, Bedford, Mass.

An SDS-PAGE gel was copper stained with Bio-Rad from Hercules, Calif. The $Ste20_{trunc}$ band (~80 kDa) was cut out, destained, washed, digested in-gel with trypsin, and the tryptic peptides extracted. HPLC separations (Michrom UMA, Michrom BioResources, Inc., Pleasanton, Calif.)

were made with a C8 silica gel column (Inertsil C8 (150 mm×0.7 mm, 5 um, 300 Å) GL Science, Tokyo, Japan). The eluent from the HPLC column was connected directly to the electrospray ion source. Mobile phase A was acetonitrile:water (2:98 (v/v)) containing 0.1% TFA and mobile phase B was acetonitrile:water (95:5) containing 0.7% TFA. A linear gradient program was run from 0 to 60% B over a period of 60 minutes (flow-rate 20 µl/min).

Ten percent of the sample was used for MALDI-TOF-MS analysis and the other 90% for LC-MS and LC-MS/MS analysis to identify sites which were phosphorylated. LC-MS and LC-MS/MS analysis were performed with an electrospray ion trap mass spectrometer, model LCQ, available from Finnigan MAT, San Jose, Calif., operated in a mode which alternated single mass spectral ("ms") scans (m/z 400–2000) with ms/ms scans (data dependent scan mode in which the most intense ion peak in the previous ms scan was isolated and subjected to collision-induced dissociation ("CID")). The CID energy was set at 30 and the ion injection time at 100 ms. The MALDI analysis was conducted as described above in Example 2.

MALDI-TOF-MS and LC-ESI-ion trap-MS/MS analysis of unlabeled full length Ste20 as well as a truncated form spanning residues 496–939 (Ste20$_{trunc}$) identified 13 sites that were phosphorylated in vivo: Ser$^{418}$ (Ser$^{422}$ or Thr$^{423}$), Ser502, three sites in a tryptic peptide spanning residues 506–530, Ser$^{547}$ (Ser$^{521}$, Thr$^{552}$ or Thr$^{555}$), Ser$^{562}$, Thr$^{573}$, Ser$^{585}$, Thr$^{773}$, and (Ser$^{861}$ or Thr$^{863}$). The ambiguities in the identification of certain of the sites arise because MS/MS analysis does not always provide information on each amino acid residue in the peptide sequence.

To monitor the differences in phosphorylation of STE20$_{trunc}$ in CLN2$^+$ versus cln2$^-$, two cell pools were prepared. One cell pool contained CLN2$^+$ in a medium containing a natural abundance of $^{14}$N and the other cell pool contained cln2$^-$ in a medium enriched in $^{15}$N. The media for each cell pool were prepared as described above in Example 2. Fractions from the two cell pools were mixed and subjected to SDS-PAGE. The band containing the mixture of labeled and unlabeled STE20$_{trunc}$ was excised and digested with trypsin. The resulting peptides were extracted by HPLC on a Michrom UMA instrument with a pre-column splitter and 50 mm×0.2 mm C18 silica gel capillary column. The capillary column used was the Magicms, 200 Å, 5 um, available from Michrom BioResources, Inc. Mobile phase A was methanol:water (5:95) containing 1.0% acetic acid, and mobile phase B was methanol:water (85:15) containing 1.0% acetic acid. A linear gradient program was carried out from 0 to 60% of B concentration for 30 minutes. The total flow-rate was 50 µl/min prior to pre-column splitting and ~3 µl/min after splitting. The total event was directed to an electrospray ion trap mass spectrometer, which was operated in single-stage MS profile mode over the range of m/z 400–2000 with an ion injection time of 100 ms. The mass spectrometer was a Finnigan LCQ electrospray ion trap spectrometer, available from Finnigan MAT, San Jose, Calif.

Figure 11:
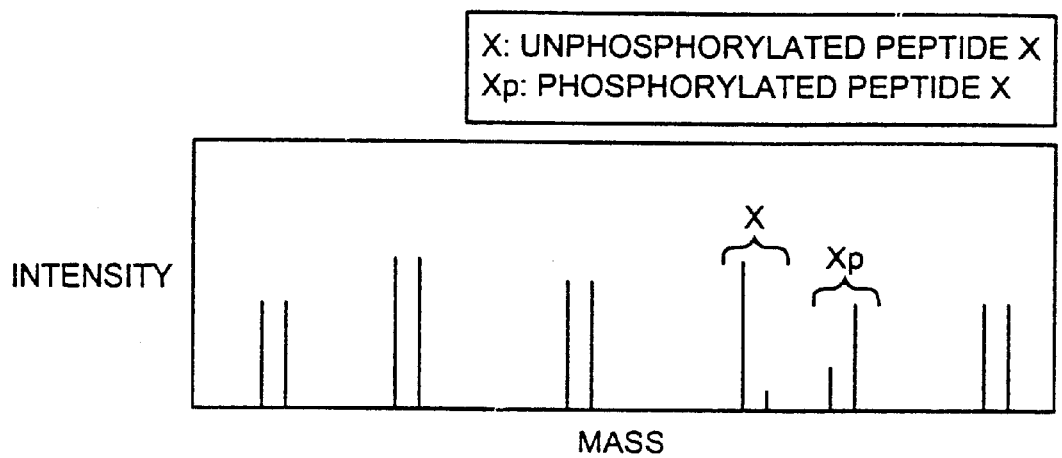
FIG. 11 is a schematic representation of a mass spectrum, indicating a plurality of pairs of peaks, including a pair of peaks corresponding to a unphosphorylated peptide (X) and a pair of peaks corresponding to the same peptide, which has been phosphorylated ($X_p$)
Figure 12:
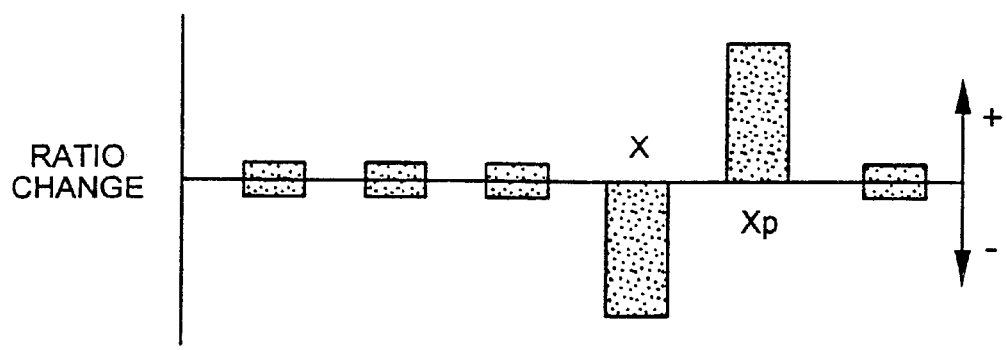
FIG. 12 is bar graph showing the changes in the ratios of the unphosphorylated peptide X and the phosphorylated peptide $X_p$.

FIG. 11 is a schematic representation of the resulting mass spectrum. For the purpose of illustration, peptides that remain unchanged in the two cell pools are assumed to be present in equal abundance and the level of phosphorylation of peptide X is assumed to change from 30% (pool 1) to 70% (pool 2)—leading to a decrease in the measured intensity ratio of unphosphorylated peptide X and an increase for phosphorylated peptide ($X_p$). FIG. 12 shows the actual changes in the ratios for the unphoshorylated peptide X and the phosphorylated peptide $X_p$.

Measurement of the intensity ratios of the isotopically labeled (cln2$^-$) versus unlabeled (CLN2$^+$) phosphopeptides showed that at least four of these sites exhibited large increases in phosphorylation in the CLN2$^+$ cell pool. These Cln2-dependent sites appear to be consensus cyclin dependent S/T-P sites, consistent with direct phosphorylation of Ste20 by Cln2–Cdc28.

Figure 13:
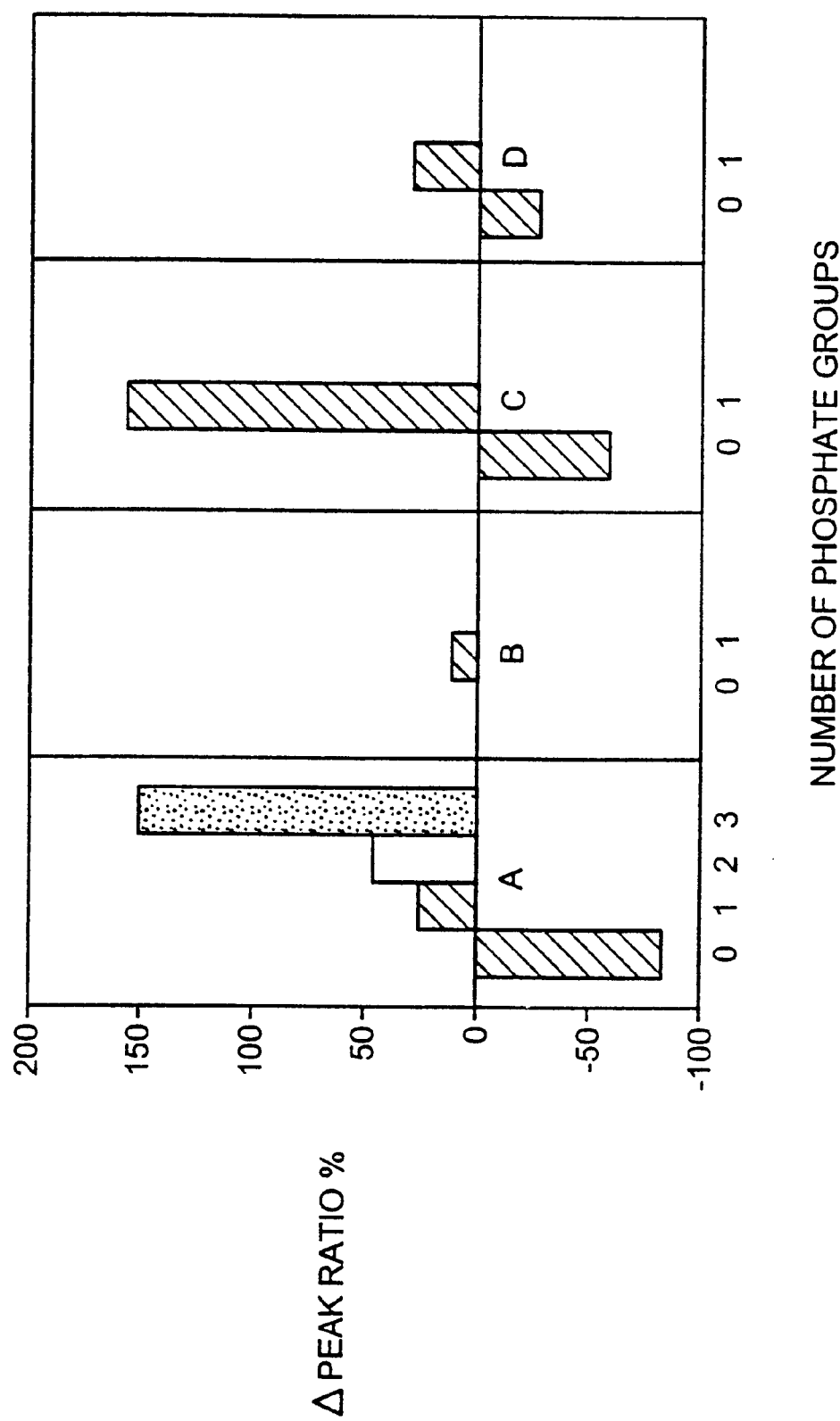
FIG. 13 shows the experimentally observed change of the intensity ratio of the unphosphorylated peptide as well as the change observed for the singly, doubly and triply phosphorylated Ste20 peptide obtained from $CLN2^+$ versus $cln2^-$ cells.

It was found that the Ste20 peptide SKT<u>SP</u>IISTAH<u>TP</u>QQAQ<u>SP</u>K$^{564}$ [Sequence ID. No. 2] was phosphorylated at Ser$^{547}$, Ser$^{562}$ and (Thr$^{551}$, Ser$^{552}$, or Thr$^{555}$). The first two sites are within SP motifs (underlined) while the third site was constrained to a 5-residue stretch that contains a TP motif (underlined). FIG. 13, Box A shows the actual change in the intensity ratio of the unphosphorylated peptide X as well as the change observed for the singly, doubly and triply phosphorylated Ste20 peptide obtained from CLN2$^+$ versus cln2$^-$ cells. The intensity ratio for the unphosphorylated peptide X decreased by 84±5% while that for the singly, doubly and triply phosphorylated sites increased by 24±12%, 44±14%, and >150%, respectively, showing that phosphorylation is enhanced at all three sites in the CLN2$^+$ versus the cln2$^-$ mutant cells. By contrast, the Ste20 phosphopeptide SLSKELNEK$^{591}$ [Sequence ID. No. 4] (phosphorylated on Ser$^{585}$) undergoes no significant ratio change (9±13%, FIG. 13, Box B), demonstrating that phosphorylation at Ser$^{585}$ is not Cln2-dependent—in accord with the absence of a proline-directed kinase phosphorylation motif. Cln2-dependent phosphorylation was also observed in the peptide $^{565}$APAQETVT<u>TP</u>TSKPAQAR$^{582}$ [Sequence ID. No. 4] (FIG. 13, Box C) and to a lesser extent in the peptide$^{772}$TTMVGTPYWMAPEVVSR$^{788}$ [Sequence ID. No. 5] (FIG. 13, Box D). Using MS/MS analysis, we found the former to be phosphorylated on Thr$^{573}$ (a TP motif), while the latter peptide was phosphorylated on Thr$^{773}$ (and not Thr$^{777}$Pro$^{778}$, as was previously reported in Wu et al., J. Biol. Chem. 270, 15984 (1995)). These data demonstrate that the present method can precisely discern site-specific changes in the degree of phosphorylation of a protein.

Any post-translational modification of a protein which will effect the mass of the protein may be similarly compared.

The method of the present invention is applicable to a wide range of areas. The effective quantification of protein expression levels using the method of the present invention aids in understanding the interaction of gene expression with external factors in producing phenotypes. In combination with, and as an extension of genomic transcriptional expression mapping, the quantitative description of the protein phenotype assists in understanding the molecular basis of physiological and pathological processes.

In accordance with the present invention, changes in the post-translational expression of a protein or proteins with time may be studied by periodically withdrawing samples from a control cell pool and a cell pool whose metabolism has been arrested, either one of which may be isotopically labeled.

The effects of chemical compounds on the post-translational expression of proteins in one cell pool may be compared with a cell pool which has not been exposed to the compound. Such a procedure could be useful in screening drug candidates by giving an indication of side effects. For example, one cell pool can be treated with a compound which is a potential drug candidate. Comparison with an untreated control cell pool in accordance with the present invention can indicate the changes in post-translational protein expression caused by the drug. If it is found that the drug causes a known change in the expression of protein or proteins which is known to be deleterious, that compound can be eliminated from further development prior to the commitment of significant resources. Similarly, if it is known that a change in the expression of a protein or proteins has a positive effect, a comparison of those protein levels in the treated and control pool in accordance with the method of the invention can give a preliminary determination of whether a particular compound may be a useful drug.

With a knowledge of the deleterious and positive changes in protein expression, the toxicology of pesticides, chemicals and environmental agents can also be examined in accordance with the method of the present invention. In the field of agriculture, the effects of fertilizers, pesticides and pheromones on the post-translational synthetic expression of proteins can be studied.

The effects of gene therapy can also be studied by the methods of the present invention. One or more genes in the cells in one cell pool can be inserted, replaced, modified, overexpressed or underexpressed, as is known in the art. In accordance with the present invention, a control cell pool in which the genes have not been subjected to gene therapy is provided, as well. Either one of the cell pools can be cultured in an isotopically enriched or depleted medium while the other is cultured in a medium having naturally occurring isotopic proportions. The method of the present invention enables the effects of such a genetic modification on post translational protein expression or other cellular functions to be studied.

The effects of treatments on the cell membranes themselves can also be studied in accordance with the present invention. In this case, isotopically enriched and non-isotopically enriched cell pools are combined, the cell membranes are removed from the combined cell pool in a manner known in the art, digested and subjected to mass spectroscopy.

The secreted by-products of the cell pools could also be compared by drawing samples from the media of each pool, one of which is isotopically enriched, mixing the samples, removing the cells and any other unwanted components, and analyzing the remaining mixture of the sample media by mass spectroscopy, as described above.

The post-translational effects of hormones, infectious agents such as viruses and bacteria, carcinogens, and trauma, such as burns, can be similarly studied and quantified. Pain modulation can also be examined.

The effects of cell differentiation on post-translational protein expression can also be studied in accordance with the method of the present invention.

The applications described herein are merely examples of several of the many possible uses of the process of the present invention. While the present invention has been described with respect to quantifying post-translational changes in protein expression, changes in protein expression resulting from the effects of any modulation on translation or transcription can also be studied and quantified. In addition, the process of the present invention may be used to compare the relative quantities of any biological component which can be ionized or whose subcomponents can be ionized so that it can be analyzed by mass spectroscopy, in any type of biological matter which can be grown in an isotopically labeled medium. For example, in addition to the proteins and peptides discussed above, the biological component may be a nucleic acid, a carbohydrate, a lipid, a cofactor and post-synthetic derivatives thereof.

In addition to the biological cells discussed above, the biological matter itself may be a microbiological culture, biological tissue, an organ, an organism, a collection of organisms, a part of an organism, and a cell-free biological mimetic system, for example.

The biological component can also act as a marker for effects on biological processes. For example, if it is known that the level of a protein changes due to a change in a biological process caused by a modulation, the change in that protein level can be used to study the response of the biological process to the modulation even if the role of that protein in that process is not understood. A marker could be any biological component.

As an example of the comparison of the effects of a modulation on the characteristics of organisms, two cultures of nematodes can be grown, one in a medium containing a normal abundance of isotopes and the other in a medium isotopically enriched or depleted in at least one isotope. One of the cultures may then be modulated. The cultures can then be mixed, the nematodes broken up, such as by crushing, and a portion of the combined culture extracted and subjected to mass spectroscopy to analyze the differential effect of the modulation on the nematodes from each cell pool.

Cells, tissue, fluids or other biological matter may also be withdrawn from a human or animal subject fed isotopically enriched or depleted food for comparison with the same biological matter withdrawn from another human or animal subject fed food having normal isotopic proportions, and analyzed in accordance with the present invention. Biological matter withdrawn from different species of animals can also be compared in accordance with the present invention to study the differences in protein expression, and other differences, between the species.

Samples from the same human or animal subject can be analyzed at different points in time, as well. First, biological matter such as cells, tissues or fluids are withdrawn from the subject. Then the subject is fed food enriched in one or more isotopes. After sufficient time for metabolism, the same biological matter is withdrawn from the subject. The withdrawn materials are mixed and analyzed as described above. Samples can be withdrawn at multiple times to monitor the metabolism of the food with time, as well. Such analyses may be useful in clinical investigation and diagnosis.

As mentioned above, one of the samples of biological matter need not be cultured, grown or maintained in a medium or food having a normal abundance of isotopes. As long as the abundance of at least one isotope in one of the media or the food fed one of the animals is different from the abundance of that isotope in the other, the method of the present invention may be applied.

We claim:

1. A method for determining the relative abundance of a protein of interest in multiple samples of biological matter comprising:

(i) culturing a first cell pool in a first medium containing an abundance of at least one isotope;

(ii) culturing a second cell pool in a second medium having a different abundance of the isotope;

(iii) modulating one of the cell pools;

(iv) combining at least a portion of each of the cell pools to obtain a combined cell pool;

(v) extracting proteins from the combined cell pool to obtain a mixture of proteins;

(vi) separating the protein of interest from the mixture of proteins;

(vii) subjecting the protein to mass spectroscopy; and (viii) computing a ratio between peak intensities of the protein to determine the relative abundance of the protein of interest from each cell pool.

2. The method of claim 1, wherein the separating step is carried out by a process selected from the group consisting of one-dimensional electrophoresis, two-dimensional electrophoresis, ultra-centrifugation, chromatography and affinity binding.

3. The method of claim 1, wherein the modulating of step (iii) comprises subjecting the biological matter in the first cell pool to an environmental or chemical stimulus.

4. The method of claim 1, wherein the modulating of step (iii) comprises genetically manipulating the biological matter in the first cell pool.

5. The method of claim 4, wherein the genetic manipulation comprises performing gene therapy.

6. The method of claim 1, wherein the modulating of step (iii) comprises subjecting one of the cell pools to a drug or hormone.

7. The method of claim 1, wherein the modulating of step (iii) comprises subjecting the cell pool to treatment chosen from the group consisting of a virus, a bacteria and a carcinogen.

8. The method of claim 1, wherein the protein is a marker for the effect of the modulating step on a biological process.

9. The method of claim 1, comprising culturing the second cell pool in a second medium in which the at least one isotope is non-radioactive.

10. The method of claim 1, comprising culturing the second cell pool in a second medium enriched in the at least one isotope.

11. The method of claim 1, comprising culturing the second cell pool in a second medium depleted in the at least one isotope.

12. A The method of claim 1, wherein the biological matter is chosen from the group consisting of biological cells, biological tissue, an organ, and organism, a collection of organisms, a portion of an organism, and a cell-free biological mimetic system.

13. The method of claim 1, comprising culturing the second cell pool in a second medium wherein at least one isotope chosen from the group consisting of nitrogen-15, carbon-13, oxygen-17, oxygen-18, sulfur-34 and hydrogen-2, has a different abundance than the abundance of the same isotope in the first medium.

14. The method of claim 1, comprising culturing the second cell pool in a second medium wherein at least one isotope is nitrogen-15.

15. The method of claim 14, comprising culturing the second cell pool in a second medium enriched to at least about 90% in nitrogen-15.

16. A method for determining the relative abundance of a protein of interest in multiple samples of biological matter, each sample comprising at least three different proteins, the method comprising:

(i) culturing a first cell pool in a first medium containing an abundance of at least one isotope;

(ii) culturing a second cell pool in a second medium having a different abundance of the isotope;

(iii) modulating one of the cell pools;

(iv) combining at least a portion of each of the cell pools to obtain a combined cell pool;

(v) extracting proteins from the combined cell pool to obtain a mixture of proteins;

(vi) separating the at least three proteins from the mixture of proteins;

(vii) subjecting the at least three proteins to mass spectroscopy; and (viii) computing a ratio between peak intensities of the at least three proteins;

(ix) comparing the ratios to determine the relative abundance of the protein of interest from each cell pool.

* * * * *

UNITED STATES PATENT AND TRADEMARK OFFICE
CERTIFICATE OF CORRECTION

PATENT NO.    : 6,642,059 B2
DATED         : February 17, 2004
INVENTOR(S)   : Chait et al.

It is certified that error appears in the above-identified patent and that said Letters Patent is hereby corrected as shown below:

<u>Column 16,</u>
Line 29, now reads "Ste$^{20}$", and should read -- Ste20 --.

Signed and Sealed this

Thirtieth Day of March, 2004

JON W. DUDAS
*Acting Director of the United States Patent and Trademark Office*

SEQUENCE LISTING

<160> NUMBER OF SEQ ID NOS: 5

<210> SEQ ID NO 1
<211> LENGTH: 108
<212> TYPE: PRT
<213> ORGANISM: Human

<400> SEQUENCE: 1

Gly Ser Gly Asn Ser Leu Glu Lys His Ser Trp Tyr His Gly Pro Val

-continued

```
                1               5                  10                 15
Ser Arg Asn Ala Ala Glu Tyr Leu Leu Ser Ser Gly Ile Asn Gly Ser
                        20                  25                 30

Phe Leu Val Arg Glu Ser Glu Ser Ser Pro Gly Gln Arg Ser Ile Ser
            35                  40                  45

Arg Tyr Glu Gly Arg Val Tyr His Tyr Arg Ile Asn Thr Ala Ser Asp
        50                  55                  60

Gly Lys Leu Tyr Val Ser Ser Glu Ser Arg Phe Asn Thr Leu Ala Glu
 65                 70                  75                     80

Leu Val His His His Ser Thr Val Ala Asp Gly Leu Ile Thr Thr Leu
                    85                  90                  95

His Tyr Pro Ala Pro Lys Arg Gly Ile His Arg Asp
                100                 105

<210> SEQ ID NO 2
<211> LENGTH: 20
<212> TYPE: PRT
<213> ORGANISM: Saccharomyces cerevisiae

<400> SEQUENCE: 2

Ser Lys Thr Ser Pro Ile Ile Ser Thr Ala His Thr Pro Gln Gln Ala
 1               5                  10                  15

Gln Ser Pro Lys
            20

<210> SEQ ID NO 3
<211> LENGTH: 9
<212> TYPE: PRT
<213> ORGANISM: Saccharomyces cerevisiae

<400> SEQUENCE: 3

Ser Leu Ser Lys Glu Leu Asn Glu Lys
 1               5

<210> SEQ ID NO 4
<211> LENGTH: 18
<212> TYPE: PRT
<213> ORGANISM: Saccharomyces cerevisiae

<400> SEQUENCE: 4

Ala Pro Ala Gln Glu Thr Val Thr Thr Pro Thr Ser Lys Pro Ala Gln
 1               5                  10                  15

Ala Arg

<210> SEQ ID NO 5
<211> LENGTH: 17
<212> TYPE: PRT
<213> ORGANISM: Saccharomyces cerevisiae

<400> SEQUENCE: 5

Thr Thr Met Val Gly Thr Pro Tyr Trp Met Ala Pro Glu Val Val Ser
 1               5                  10                  15

Arg
```